(12) United States Patent
Galantai

(10) Patent No.: US 12,390,840 B2
(45) Date of Patent: Aug. 19, 2025

(54) CLEANING DEVICE

(71) Applicant: IPH Limited, Auckland (NZ)

(72) Inventor: Roderick Francis Galantai, Auckland (NZ)

(73) Assignee: IPH Limited, Auckland (NZ)

( * ) Notice: Subject to any disclaimer, the term of this patent is extended or adjusted under 35 U.S.C. 154(b) by 870 days.

(21) Appl. No.: 17/359,174

(22) Filed: Jun. 25, 2021

(65) Prior Publication Data

US 2021/0402448 A1 Dec. 30, 2021

Related U.S. Application Data

(60) Provisional application No. 63/043,786, filed on Jun. 25, 2020.

(51) Int. Cl.
*B08B 9/04* (2006.01)
*B08B 9/043* (2006.01)
*B08B 9/055* (2006.01)

(52) U.S. Cl.
CPC ............ *B08B 9/0436* (2013.01); *B08B 9/04* (2013.01); *B08B 9/0557* (2013.01)

(58) Field of Classification Search
CPC ......... A61B 1/122; B08B 9/04; B08B 9/0557; B08B 9/0436
See application file for complete search history.

(56) References Cited

U.S. PATENT DOCUMENTS

| 387,410 A | 8/1888 | Gillette |
| 449,080 A | 3/1891 | Mackay |
| 3,939,519 A | 2/1976 | Muirhead |
| 4,178,649 A | 12/1979 | Herzog et al. |
| 4,700,423 A | 10/1987 | Zuliani |
| 5,457,841 A * | 10/1995 | Minton ................. B08B 9/0557 15/104.061 |
| 5,882,329 A | 3/1999 | Patterson et al. |
| 5,960,505 A * | 10/1999 | Sanghoon ............. B08B 9/0557 15/104.16 |
| 6,145,150 A * | 11/2000 | Knapp ................. B08B 9/0557 15/104.061 |

(Continued)

FOREIGN PATENT DOCUMENTS

| EP | 3136944 B1 | 3/2020 |
| JP | H 08-173379 | 7/1996 |

(Continued)

OTHER PUBLICATIONS

International Search Report and Written Opinion from PCT/IB2021/055709, dated Nov. 22, 2021, 14 pages.

(Continued)

*Primary Examiner* — Michael D Jennings
(74) *Attorney, Agent, or Firm* — BAKERHOSTETLER

(57) ABSTRACT

Cleaning devices described herein can provide a hybrid fin and wiper system to facilitate removal of residual solids and liquids from a tubular device (e.g., endoscope), even in a single pass. The cleaning devices described herein can provide pressure equalization and release to effectively clean a blind channel without causing hydraulic compaction of debris. The cleaning devices described herein can provide a connection system that facilitates adjustment and customization based on the needs of a particular application.

19 Claims, 22 Drawing Sheets

(56) References Cited

U.S. PATENT DOCUMENTS

| | | | |
|---|---|---|---|
| 6,276,017 B1* | 8/2001 | Lino | B08B 9/0557 15/104.063 |
| 6,792,641 B1 | 9/2004 | Laker | |
| 6,889,402 B2 | 5/2005 | Galantai | |
| 7,959,740 B2 | 6/2011 | Cevallier | |
| 8,051,523 B1* | 11/2011 | Franzino | B08B 9/0557 15/104.061 |
| 8,256,057 B2* | 9/2012 | Galantai | B08B 9/0436 15/104.16 |
| 8,584,297 B2 | 11/2013 | Tash | |
| 8,793,918 B2* | 8/2014 | Rogers | F41A 29/02 42/95 |
| 8,850,650 B2* | 10/2014 | Borsari | A46B 3/18 132/218 |
| 9,579,012 B2 | 2/2017 | Vazales et al. | |
| 9,968,247 B2* | 5/2018 | Kaye | A61B 1/122 |
| 10,349,821 B2 | 7/2019 | Gunday et al. | |
| 11,098,557 B2* | 8/2021 | Hoffman | E21B 33/16 |
| 2008/0200101 A1* | 8/2008 | Chevallier | B24D 15/04 451/340 |
| 2010/0012152 A1 | 1/2010 | Hansen | |
| 2012/0017386 A1* | 1/2012 | Rankin | B08B 9/0557 15/104.061 |
| 2013/0139850 A1 | 6/2013 | Axelsson et al. | |
| 2017/0037605 A1* | 2/2017 | Elliott | E03C 1/302 |
| 2017/0216890 A1 | 8/2017 | Seltz | |
| 2017/0356715 A1* | 12/2017 | Bartlett | B08B 9/0436 |
| 2018/0066420 A1* | 3/2018 | Beck | B25G 1/102 |
| 2018/0080304 A1* | 3/2018 | Cortez | E21B 17/1014 |
| 2018/0249903 A1* | 9/2018 | Strombergsson | A61B 1/125 |
| 2020/0373137 A1* | 11/2020 | Hauschild | H01J 49/4255 |

FOREIGN PATENT DOCUMENTS

| | | | |
|---|---|---|---|
| JP | 2013-530746 | 8/2013 | |
| JP | 2017-514605 | 6/2017 | |
| WO | WO-2004012573 A2 * | 2/2004 | A61B 1/122 |

OTHER PUBLICATIONS

Japanese Patent Application No. 2022-580475; Office Action dated Aug. 26, 2025, 7 pages with English language translation.

* cited by examiner

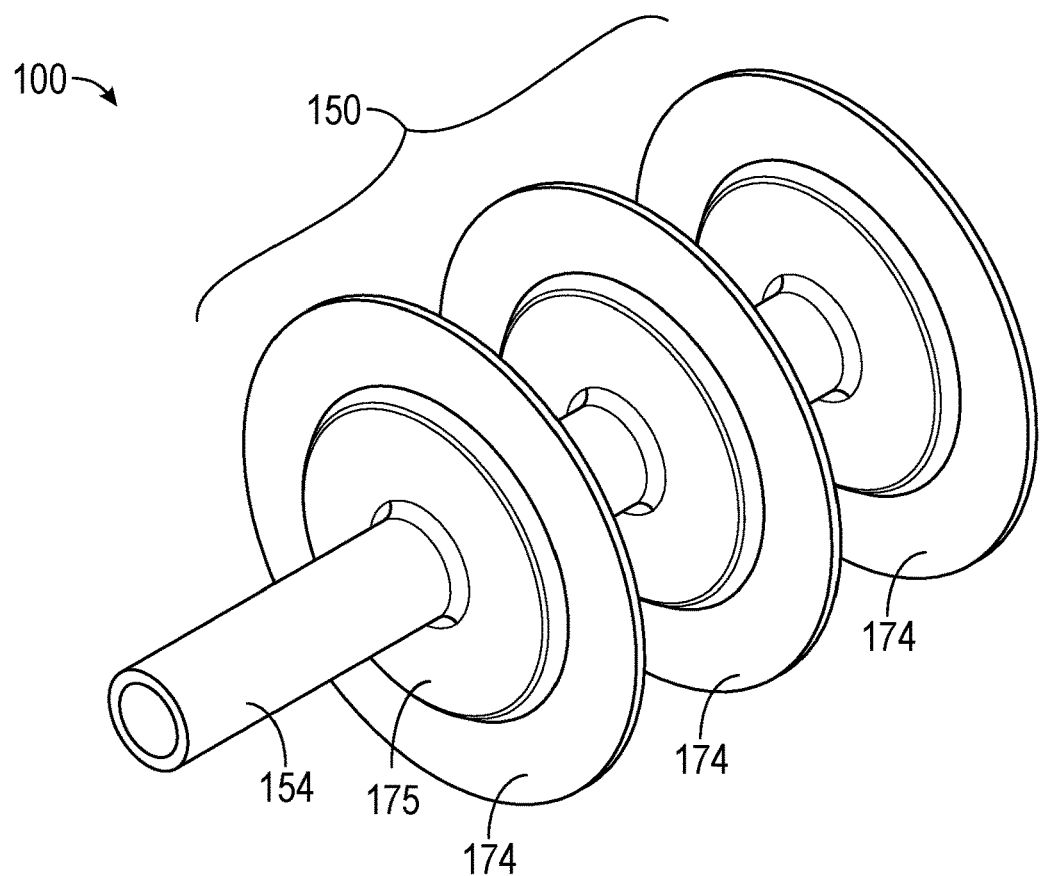
FIG. 15
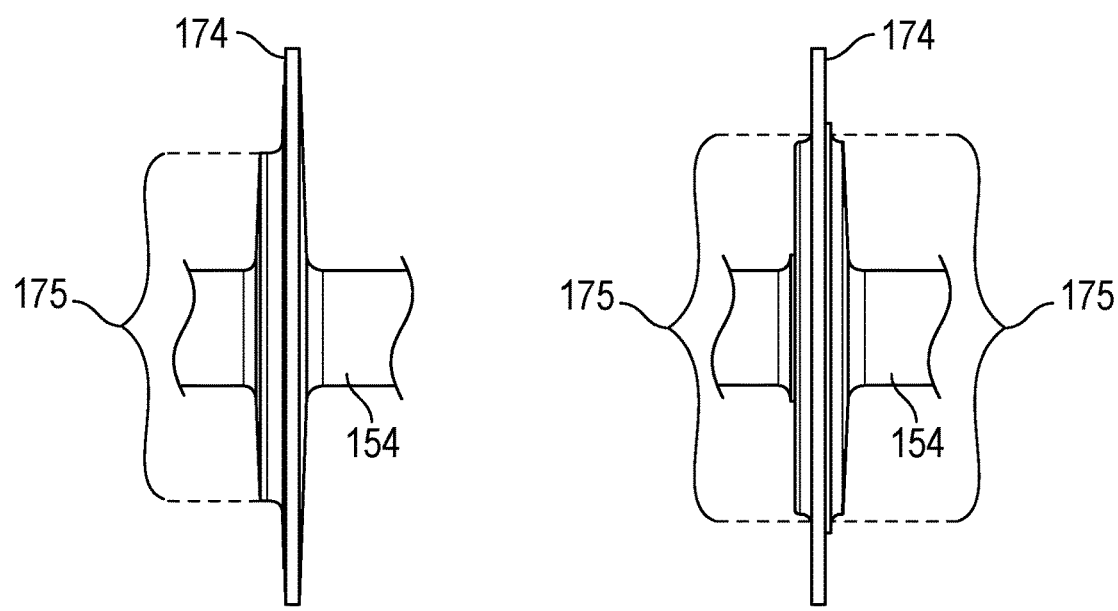
FIG. 16  FIG. 17

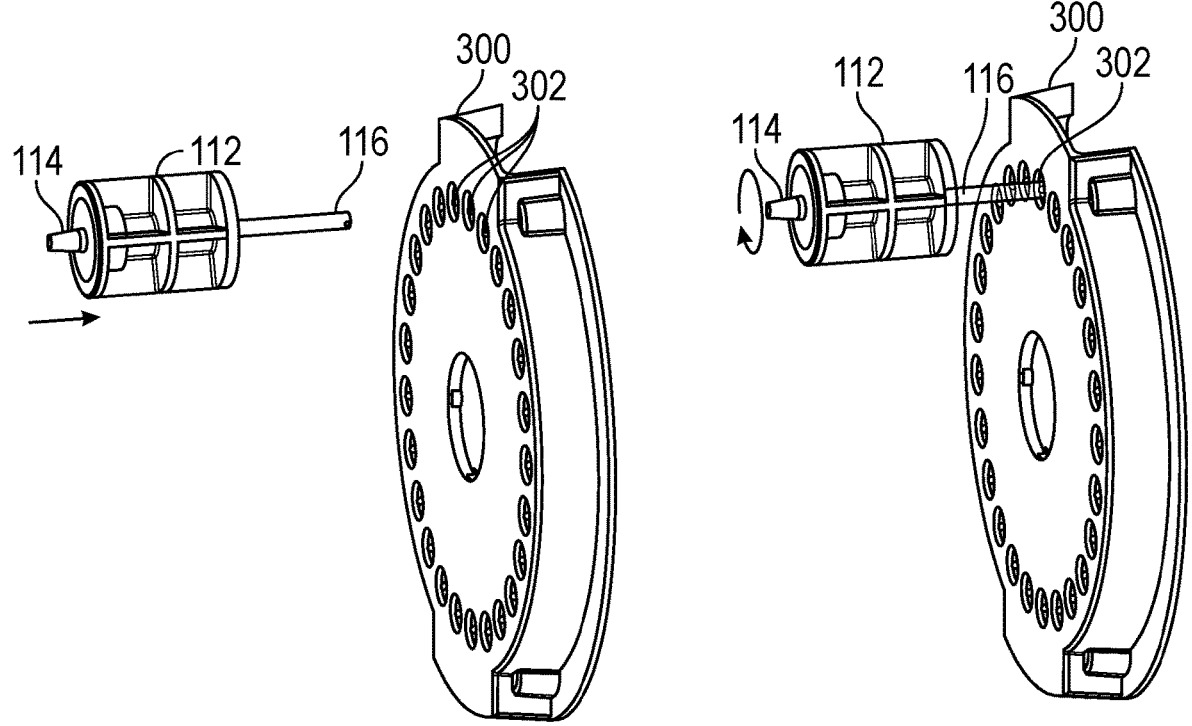
FIG. 43   FIG. 44
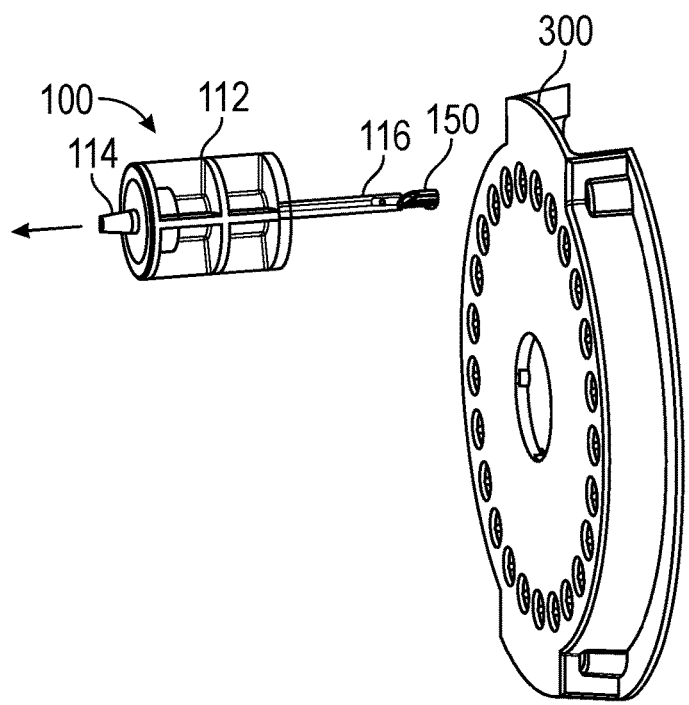
FIG. 45

CLEANING DEVICE

CROSS-REFERENCE TO RELATED APPLICATION

This application claims the benefit of U.S. Provisional Application No. 63/043,786, entitled "CLEANING DEVICE," filed Jun. 25, 2020, the entirety of which is incorporated herein by reference.

TECHNICAL FIELD

The present description relates generally to cleaning devices and, more particularly, to pull and/or push through cleaning devices and related methods of manufacture and use.

BACKGROUND

Endoscopes and other medical devices require frequent cleaning to allow subsequent and safe use. It has been found that endoscopes (such as those lined with, for example, a polymer sleeve) can be effectively high-level disinfected or sterilized between uses by a cleaning regime that involves the pushing and/or pulling through of a brush. The effect of such actions is to smooth and remove soil from the inwardly directed surface and surface deposits of the polymer sleeve or other structure defining a radially innermost surface. This can better facilitate mechanical and chemical cleaning and subsequent sterilization.

BRIEF DESCRIPTION OF THE DRAWINGS

Certain features of the subject technology are set forth in the appended claims. However, for purpose of explanation, several embodiments of the subject technology are set forth in the following figures.

FIG. 15 shows a perspective view of a cleaning section of a cleaning device having wipers, according to some embodiments of the present disclosure.

FIG. 16 shows a side view of a portion of a cleaning device, according to some embodiments of the present disclosure.

FIG. 17 shows a side view of a portion of a cleaning device, according to some embodiments of the present disclosure.

FIG. 43 shows a perspective view of a cleaning device and a dispenser, according to some embodiments of the present disclosure.

FIG. 44 shows a perspective view of the cleaning device inserted into a bay of the dispenser of FIG. 43, according to some embodiments of the present disclosure.

FIG. 45 shows a perspective view of the cleaning device with a cleaning section from the dispenser of FIG. 44, according to some embodiments of the present disclosure.

DETAILED DESCRIPTION

Figure 1:
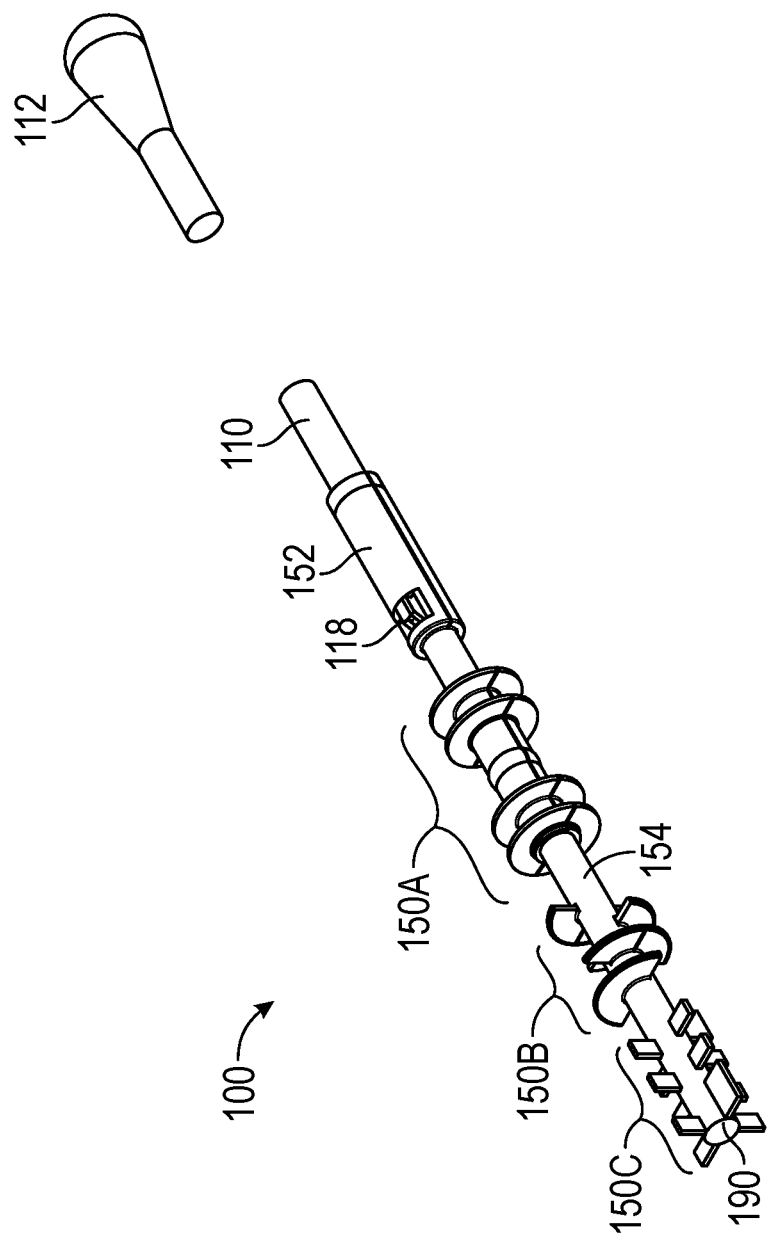
FIG. 1 shows a perspective view of a cleaning device with multiple cleaning sections, according to some embodiments of the present disclosure.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be clear and apparent to those skilled in the art that the subject technology is not limited to the specific details set forth herein and may be practiced without these specific details.

The present description relates generally to cleaning devices and, more particularly, to pull and/or push through cleaning devices and related methods of manufacture and use.

Tubular medical devices are used to treat a variety of patient conditions. Such medical devices can be used to deliver surgical tools, deliver diagnostic tools, restore airflow, inject substances, evacuate substances, and the like. Secretions and debris can accumulate on the inside wall of a tubular medical device during use. The medical devices can develop harmful bacteria and/or other matter that, if not removed in a timely and efficient manner, can be harmful to a patient. It can be important to patient health and safety to ensure that medical devices are clean prior to use in a patient. Removal of residual solids and liquids from within a tubular structure can achieve and/or facilitate effective cleaning, which may include further operations such as chemical and/or heated cleaning.

The cleaning devices described herein can provide a hybrid fin and wiper system to facilitate removal of residual solids and liquids from a tubular device (e.g., endoscope), even in a single pass. The cleaning devices described herein can provide pressure equalization and release to effectively clean a blind channel and may prevent the hydraulic compaction of debris. The cleaning devices described herein can provide a connection system that facilitates adjustment and customization based on the needs of a particular application.

While some references are made to medical devices (e.g., endoscopes) to be cleaned, it will be understood that the cleaning devices described herein can have a variety of applications and that no particular configuration described herein is limited to only one application. For example, the cleaning devices described herein can be used on any device having a tubular portion defining inner walls that define a channel that is accessible through at least one end thereof. Such devices can include tubular portions that are straight, curved, uniform in shape and/or cross-sectional dimension, variable in shape and/or cross-sectional dimension (e.g., tapered, stepped, corrugated tube, etc.), and the like. The channels of such tubular portions can optionally intersect with other channels. The channels can have an open end and, optionally, a blind (e.g., closed) end. By further example, devices to be cleaned can include medical devices, firearms, fluid and/or gas delivery conduits (e.g., fuel lines), musical instruments, culinary tools, drinking straws, testing equipment, storage containers, and the like. Examples of medical devices can include endoscopes, borescopes, tracheal tubes, catheters, and the like. It will be appreciated that the cleaning capabilities provided by the cleaning devices described herein can provide cleaning to optimize performance of any such devices for reasons that may be particular to the corresponding device.

As used herein the term "pull through" also includes (where the circumstance allows) a "push through" device. Frequently, by way of example, where a short length conduit is to be dealt with, it is sometimes convenient to push the head of a pull through type device through the device rather than thread and then pull the pull through device through the short length conduit. Accordingly the term "pull through" in the present specification and in the appended claims includes any variant capable in some circumstances of being used as a push through.

These and other embodiments are discussed below with reference to FIGS. 1-23. However, those skilled in the art will readily appreciate that the detailed description given herein with respect to these Figures is for explanatory purposes only and should not be construed as limiting.

Referring to FIG. 1, a cleaning device can provide multiple cleaning sections that each include cleaning features that provide effective cleaning when moved through a channel of a device to be cleaned.

FIG. 1 shows a perspective view of a cleaning device with multiple cleaning sections, according to some embodiments of the present disclosure. As shown in FIG. 1, a cleaning device 100 can include a control shaft 110 connected to one or more cleaning sections (e.g., a first cleaning section 150A, a second cleaning section 150B, and/or a third cleaning section 150C, etc.) positioned distal to the control shaft 110. The control shaft 110 can include a handle 112 or other proximalmost component that allows a user to pull or push the cleaning sections 150A, 150B, and 150C through a channel of a device to clean the inner surfaces thereof. The cleaning sections 150A, 150B, and 150C can include one or more features for acting upon the surface of the channel and items therein to clean the channel.

Each of the cleaning sections 150A, 150B, and 150C can include features extending from or otherwise being connected to a core member 154, which can extend longitudinally through and/or along one or more of the cleaning sections 150A, 150B, and 150C. The core member 154 can optionally extend to a terminal distal end 190 of the cleaning device 100, which can be further defined by a distalmost one of the cleaning sections (e.g., cleaning section 150C).

The control shaft 110 can include or be connected to a control shaft engagement element 118, and the cleaning sections 150A, 150B, and 150C and/or the core member 154 can include or be connected to a proximal engagement element 152. The control shaft engagement element 118 and the proximal engagement element 152 can engage each other to secure the control shaft 110 relative to the cleaning sections 150A, 150B, and 150C and/or the core member 154. For example, as shown in FIG. 1, at least a portion of the control shaft engagement element 118 can fit within at least a portion of the proximal engagement element 152 and mechanical engage (e.g., clip) therein, or vice versa. Such engagement can lock the control shaft 110 relative to the cleaning sections 150A, 150B, and 150C and/or the core member 154, such that translational and/or rotational movement of the control shaft 110 results in corresponding translational and/or rotational movement of the cleaning sections 150A, 150B, and 150C and/or the core member 154.

Additional or alternative mechanisms can be provided to lock the control shaft 110 with respect to the cleaning sections 150A, 150B, and 150C and/or the core member 154. For example, mechanisms such as locks, latches, snaps, screws, clasps, threads, magnets, pins, an interference (e.g., friction) fit, knurl presses, bayoneting, and/or combinations thereof can be included to lock the control shaft 110 with respect to the cleaning sections 150A, 150B, and 150C and/or the core member 154 when the control shaft engagement element 118 and the proximal engagement element 152 engage each other. The control shaft engagement element 118 can remain locked with respect to the proximal engagement element 152 until a release mechanism is actuated. The release mechanism can be provided in a manner that is accessible by a user. For example, the release mechanism can be provided on an outer surface of the control shaft engagement element 118 and/or the cleaning section engagement element 152. Where a locking mechanism locks the control shaft 110 with respect to the cleaning sections 150A, 150B, and 150C and/or the core member 154, the release mechanism, when actuated, can move and act upon the locking mechanism to cause it to release. For example, the release mechanism, when actuated, can release one or more locks, latches, snaps, screws, clasps, threads, magnets, pins, an interference (e.g., friction) fit, knurl presses, bayoneting, and/or combinations thereof that were previously locking the control shaft engagement element 118 to the cleaning section engagement element 152.

While three cleaning sections the cleaning sections 150A, 150B, and 150C are illustrated in FIG. 1, it will be understood that any number (e.g., 1, 2, 3, 4, 5, 6, 7, 8, 9, 10, or more than 10) of cleaning sections can be provided. It will be understood that at least one of the cleaning sections can provide at least one feature (e.g., wipers, fins, etc.) that is distinct from a feature (e.g., wipers, fins, etc.) of at least one other cleaning section, as described further herein. Any given cleaning section can be proximal to at least one other cleaning section. Any given cleaning section can be distal to at least one other cleaning section. A cleaning section can be positioned between at least two other cleaning sections.

Figure 2:
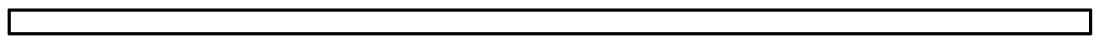
FIG. 2 shows a side view of a core member that can be used in the formation of a cleaning device, according to some embodiments of the present disclosure.
Figure 3:
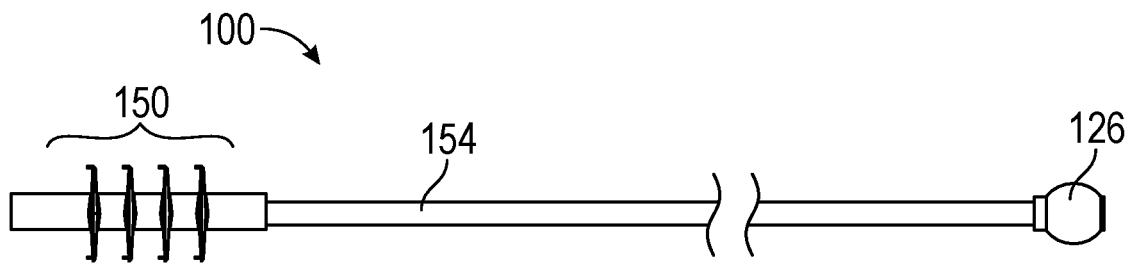
FIG. 3 shows a side view of a cleaning device including a cleaning section formed on the core member of FIG. 2, according to some embodiments of the present disclosure.

Referring to FIGS. 2 and 3, a cleaning section can be formed on a core member by, for example, an additive process that provides desired performance characteristics.

FIG. 2 shows a side view of a core member that can be used in the formation of a cleaning device, according to some embodiments of the present disclosure. The core member 154 can be or include a filament with features to allow a mechanical bond with cleaning features that are provided thereon. The core member 154 can be a monofilament or include multiple filaments. Where multiple filaments are provided, the filaments can extend in parallel, twist about each other (e.g., helically), and/or be braided together. The core member 154 can include polymer and/or metal materials and/or any one or more materials that allow for a mechanical and/or chemical bond with one or more cleaning features. The core member 154 can provide sufficient flexibility and bendability to extend through a channel, including tortuous pathways. The core member 154 can provide sufficient stiffness and rigidity to transmit forces and/or torque from a handle to cleaning sections.

FIG. 3 shows a side view of a cleaning device including a cleaning section formed on the core member of FIG. 2, according to some embodiments of the present disclosure. As shown in FIG. 3, a cleaning section 150 including one or more cleaning features can be formed over the core member 154. Additionally or alternatively, other features, such as a leader 126 can be formed on the core member 154. The cleaning section 150 and/or the leader 126 can be formed by an injection molding process, in which the features of the cleaning section 150 and/or the leader 126 are formed over a corresponding portion of the core member 154 and bonded thereto. Accordingly, the cleaning section 150 and/or the leader 126 can have a chemical and/or mechanical bond with the core member 154. The cleaning section 150 and/or the leader 126 can be formed in the same or different processes. The cleaning section 150 and/or the leader 126 can be formed from the same or different materials. The cleaning section 150 and/or the leader 126 can be formed from one or more materials that is the same as or different than the material(s) of the core member 154. For example, the core member 154 can optionally be of a harder material, and the cleaning section 150 and/or the leader 126 can be of a softer material. By further example, the core member 154 can optionally be of a softer material, and the cleaning section 150 and/or the leader 126 can be of a harder material.

Figure 4:
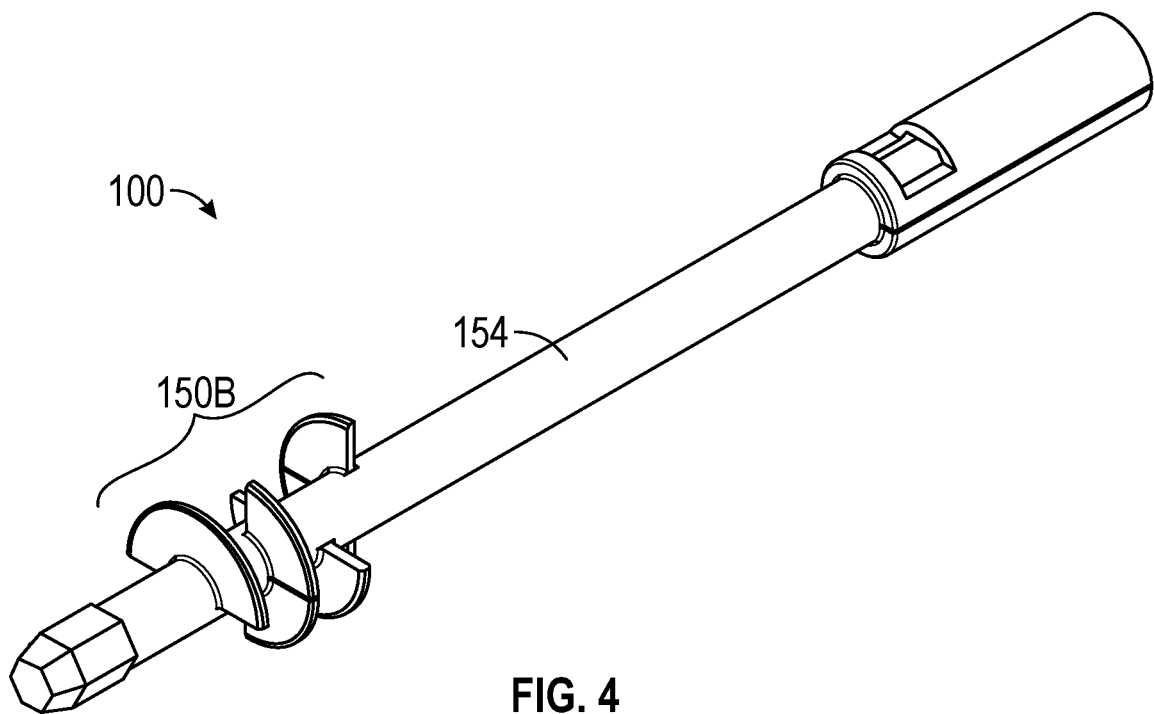
FIG. 4 shows a perspective view of a portion of a cleaning device with a cleaning section, according to some embodiments of the present disclosure.
Figure 5:
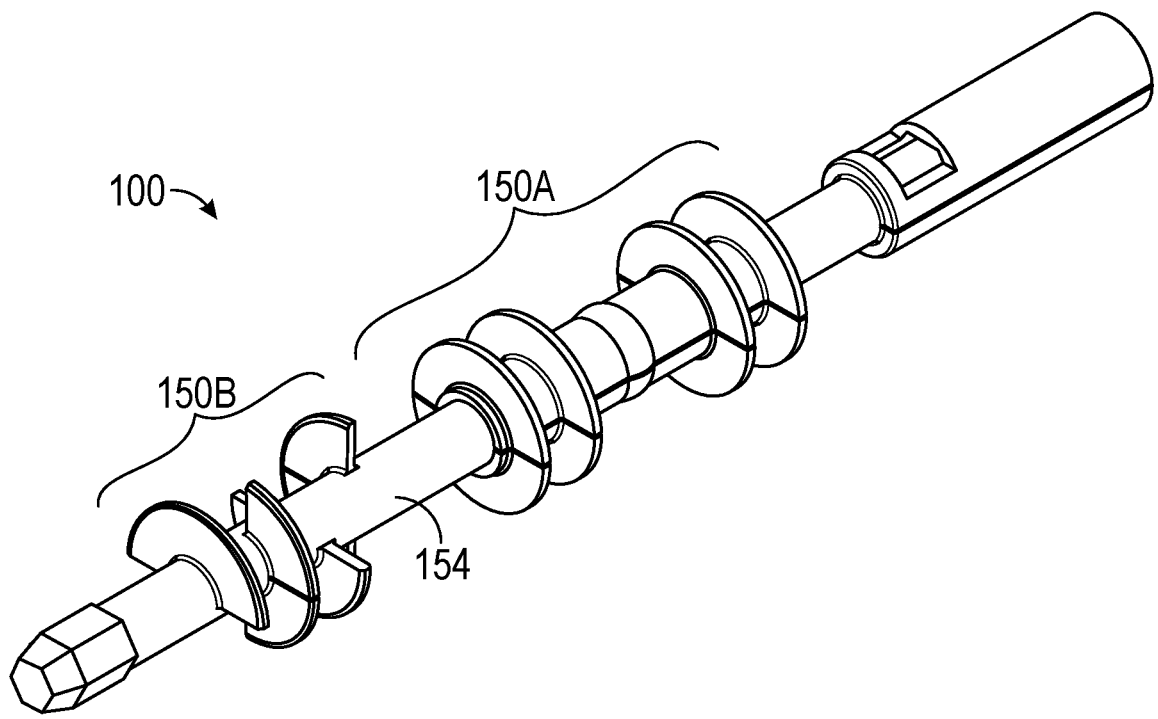
FIG. 5 shows a perspective view of the cleaning device of FIG. 4 with an additional cleaning section formed thereon, according to some embodiments of the present disclosure.

Referring to FIGS. 4 and 5, different cleaning sections can be formed on a core member by, for example, separate processes that provide desired performance characteristics in each cleaning section. For example, one cleaning section may be of a harder material to create shear on the channel wall to breakup bio-film to allow more effective chemical removal. Another cleaning section may be on a softer material to aid the formation of a seal in the channel to flush the channel with detergent.

FIG. 4 shows a perspective view of a portion of a cleaning device with a cleaning section, according to some embodiments of the present disclosure. The core member 154 and the cleaning section 150B can be formed in a single process, such as an injection molding process. For example, the core member 154 and the cleaning section 150B can be a single monolithic structure. As used herein, a monolithic structure is one that is integrally formed of a single piece of material, rather than of separate pieces that are joined together by an interface. By further example, the core member 154 and the cleaning section 150B can be a unibody and/or unitary structure. Accordingly, the core member 154 and the cleaning section 150B can be of the same material(s) and have similar characteristics (e.g., hardness).

FIG. 5 shows a perspective view of the cleaning device of FIG. 4 with an additional cleaning section formed thereon, according to some embodiments of the present disclosure. The cleaning section 150A can be formed by an injection molding process, in which the features of the cleaning section 150A are formed over a corresponding portion of the core member 154 and bonded thereto. Accordingly, the cleaning section 150A can have a chemical and/or mechanical bond with the core member 154. The cleaning section 150A can optionally be formed from one or more materials that is different than the material(s) of the core member 154 and the cleaning section 150B. For example, the core member 154 and the cleaning section 150B can optionally be of a harder material, and the cleaning section 150A can be of a softer material. By further example, the core member 154 and the cleaning section 150B can optionally be of a softer material, and the cleaning section 150A can be of a harder material. By providing the cleaning sections in different processes and with different materials, each section can have the desired cleaning characteristics (e.g., sealing, etc.) when moved through a channel of a device to be cleaned. Additionally, the core member can be provided with the desired compression and flexibility characteristics.

Referring now to FIGS. 6-15, a cleaning section can be provided with features that are distinct and provide an effective cleaning function when moved within a channel. Each of the cleaning sections described herein can be combined with any other cleaning section(s) in any arrangement to form a cleaning device. For example, any one or more of the cleaning sections described herein can be provided as one or more of the cleaning sections 150A, 150B, and/or 150C of FIG. 1, the cleaning section 150 of FIG. 3, the cleaning sections 150B of FIG. 4, and/or the cleaning sections 150A and/or 150B of FIG. 5. It will be understood that the embodiments illustrated are examples and that each cleaning device can vary from the features illustrated while still encompassing the features described herein.

Figure 6:
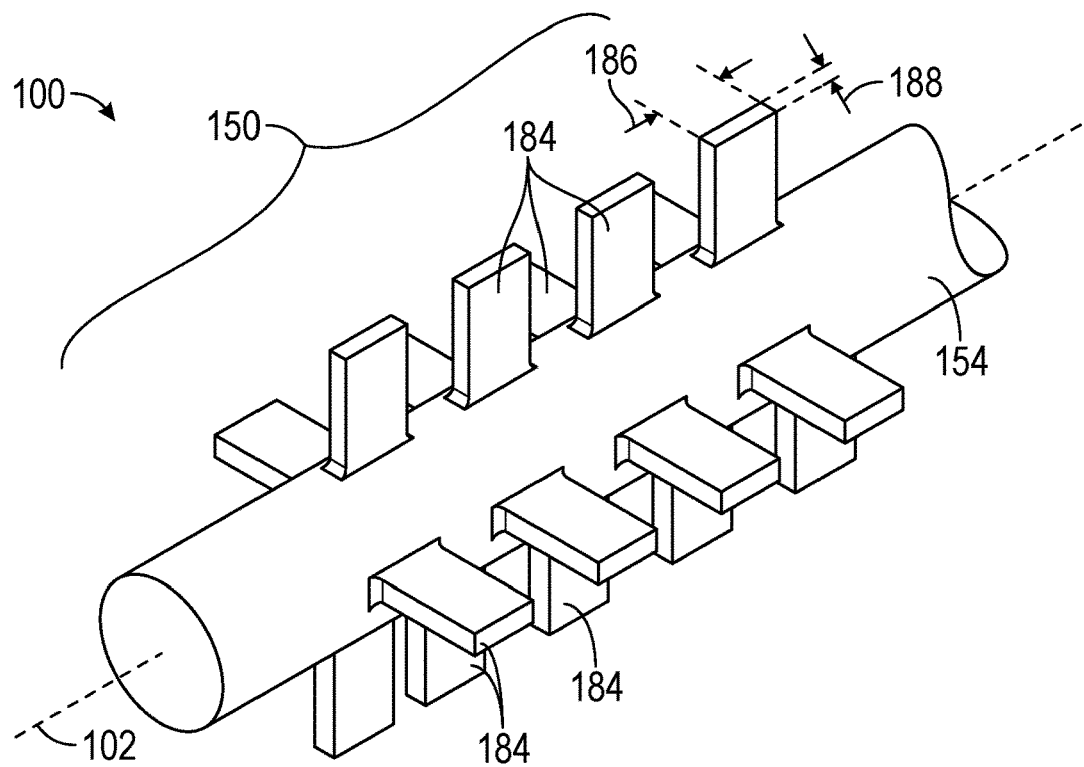
FIG. 6 shows a perspective view of a cleaning section of a cleaning device having fins, according to some embodiments of the present disclosure.

FIG. 6 shows a perspective view of a cleaning section 150 of a cleaning device 100 having fins 184, according to some embodiments of the present disclosure. As shown in FIG. 6, each one of multiple fins 184 can extend radially outwardly from a core member 154. The fins 184 can provide a cleaning function at least when the cleaning section 150 is rotated within a channel of a device. For example, the fins 184 can apply a force to materials in the channel, as well as cause turbulence of fluids within the channel.

The fins 184 can be characterized by their relative width and length. For example, as shown in FIG. 6, each of the fins 184 can have a length 186 and a width 188. Another dimension of each fin 184 can include a height to which it extends from the core member 154. As used herein, a length 186 is a dimension that is measured along (e.g., parallel to) a longitudinal axis 102 of the cleaning device 100. As used herein, a width 188 is a dimension that is measured across (e.g., orthogonal to) the longitudinal axis 102 of the cleaning device 100. Each fin 184 can have a length 186 that is greater than the width 188 thereof. Accordingly, the greater length 186 of the fins 184 provide significant longitudinal coverage as the cleaning section 150 is rotated. At the same time, the smaller width 188 of the fins 184 allows each fin 184 to bend, flex, and/or deflect as needed to avoid damaging the surface to be cleaned.

While a certain number of rows and fins are illustrated in FIG. 6, it will be understood that any number (e.g., 1, 2, 3, 4, 5, 6, 7, 8, 9, 10, or more than 10) of fins can be provided. The fins can be provided in discrete rows or otherwise distributed (e.g., helically). The fins 184 can optionally be monolithically formed with the core member 154, thereby being of the same material(s) as the core member 154. Alternatively, the fins 184 can optionally be separately formed with the core member 154 and/or be of a different material(s) than the core member 154.

The fins 184 can be distributed circumferentially, such that different fins 184 extend from the core member 154 at different circumferential positions about the longitudinal axis of the core member 154. The fins 184 can be distributed longitudinally, such that different fins 184 (e.g., in a row) extend from the core member 154 at different longitudinal positions along the longitudinal axis of the core member 154. The fins 184 can be staggered in manner that collectively provides full circumferential coverage when the cleaning section 150 is rotated. For example, while the fins 184 of any given row are longitudinally spaced apart from each other, the fins 184 of different rows can be longitudinally staggered to only partially overlap each other. Accordingly, at any given surface portion within a channel that overlaps the cleaning section 150, at least one of the fins 184 will act on the surface portion when the cleaning section 150 is rotated.

Figure 7:
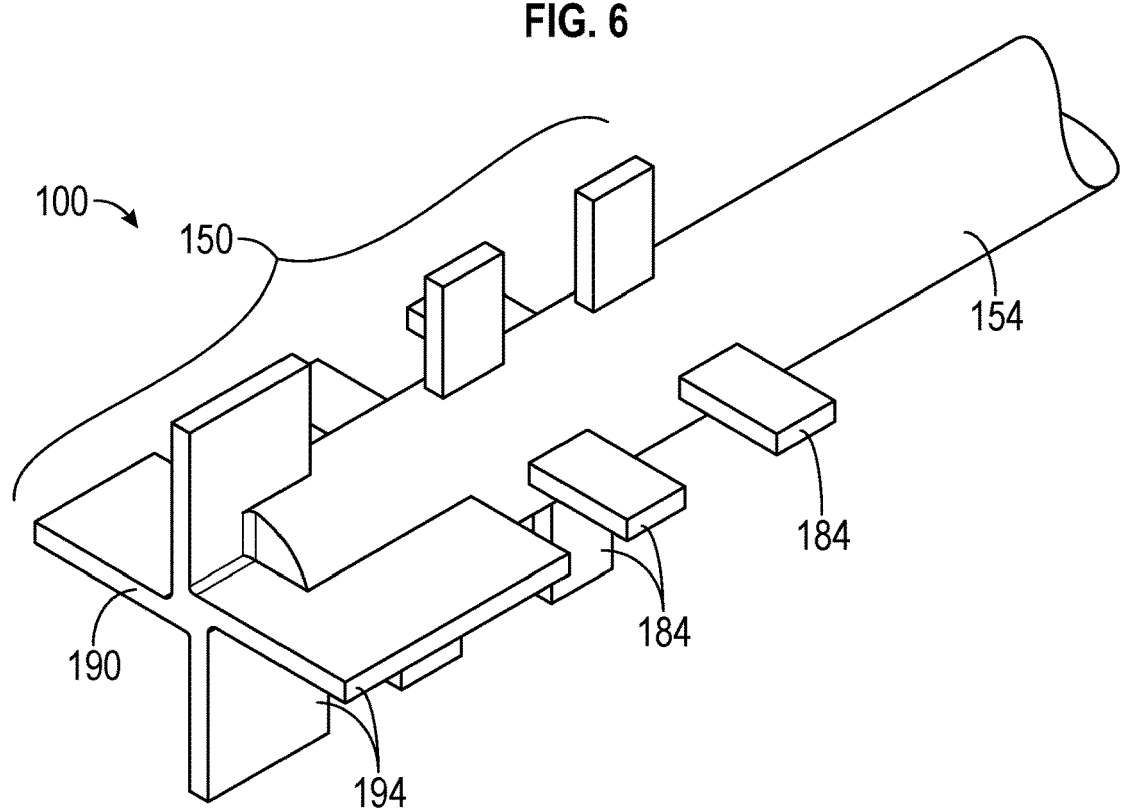
FIG. 7 shows a perspective view of a cleaning section of a cleaning device having fins forming a terminal end section, according to some embodiments of the present disclosure.

FIG. 7 shows a perspective view of a cleaning section of a cleaning device having fins forming a terminal end section, according to some embodiments of the present disclosure.

As shown in FIG. 7, the cleaning section 150 can include fins 184, similar to fins 184 of FIG. 6. However, the fins can have at least one difference, including size, shape, distribution, and/or material.

As further shown in FIG. 7, the cleaning section 150 can include terminal fins 194 that can form at least a portion of a terminal distal end 190 of the cleaning device 100. For example, the terminal fins 194 can extend beyond the core member 154 to form the terminal distal end 190. Alternatively, the terminal fins 194 and the core member 154 can both extend to the terminal distal end 190 (e.g., be flush with each other thereat). The terminal fins 194 defining at least a portion of the terminal and 190 can be useful to clean a blind (e.g., closed) end of a channel. The shape of the terminal fins 194 can be complementary to the shape of the blind end of the channel. In use, the cleaning device 100 can be advanced until the terminal fins 194 contact the blind end of the channel, and the cleaning section 150 can be rotated so that the terminal fins 194 clean both the longitudinal end of the channel and the nearby radially inner walls.

Figure 8:
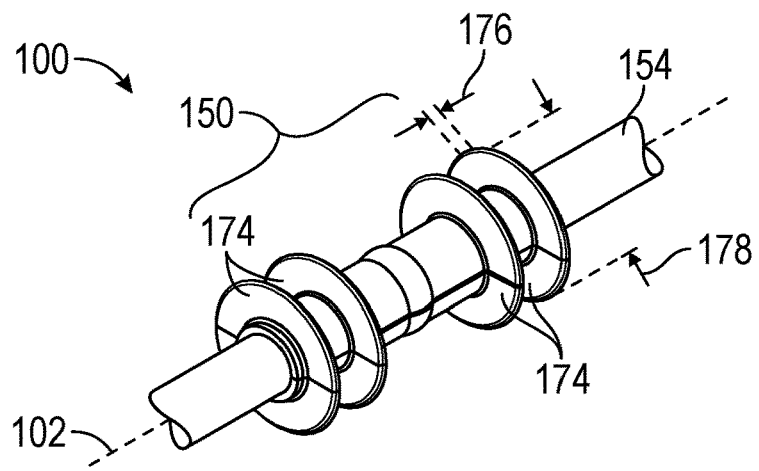
FIG. 8 shows a perspective view of a cleaning section of a cleaning device having wipers of a distinct material, according to some embodiments of the present disclosure.

FIG. 8 shows a perspective view of a cleaning section 150 of a cleaning device 100 having wipers 174, according to some embodiments of the present disclosure. As shown in FIG. 8, each one of multiple wipers 174 can extend radially outwardly from a core member 154. The wipers 174 can provide a cleaning function at least when the cleaning section 150 is moved (e.g., pulled or pushed) longitudinally within a channel of a device. For example, the wipers 174 can apply a force to materials in the channel and/or seal against the walls of the channel. The wipers 174 can optionally be separately formed on the core member 154 and/or be of different material(s) than the core member 154. Additionally or alternatively, the movement of the wipers 174 through a channel can apply a lubricant that remains thereafter, for example, within a channel of a firearm.

The wipers 174 can be characterized by their relative width and length. For example, as shown in FIG. 8, each of the wipers 174 can have a length 176 and a width 178. Another dimension of each wiper 174 can include a height to which it extends from the core member 154. Each wiper 174 can have a width 178 that is greater than the length 176 thereof. Accordingly, the greater width 178 of the wipers 174 provide significant radial and circumferential coverage as the cleaning section 150 is moved longitudinally through the channel. At the same time, the length 176 of the wipers 174 allows each wiper 174 to bend, flex, and/or deflect longitudinally as needed to avoid damaging the surface to be cleaned.

One or more of the wipers 174 can extend entirely circumferentially (i.e., 360°) about the core member 154 and/or the longitudinal axis 102 of the cleaning device 100. For example, from a given longitudinal portion of the core member 154, a wiper 174 (e.g., "full wiper") can extend in all radially outward directions on all radial sides thereof. Such a configuration can optionally provide sealing along an entire inner surface of a channel wall. Accordingly, each wiper 174 can divide the channel into separate and longitudinally adjacent portions.

The wipers 174 can be distributed longitudinally, such that different wipers 174 extend from the core member 154 at different longitudinal positions along the longitudinal axis of the core member 154. Multiple wipers can be provided for redundant cleaning functions at any given surface portion of a channel. While a certain number of wipers are illustrated in FIG. 8, it will be understood that any number (e.g., 1, 2, 3, 4, 5, 6, 7, 8, 9, 10, or more than 10) of wipers can be provided. The wipers can be evenly or unevenly distributed along the longitudinal axis. The wipers 174 can optionally be monolithically formed with the core member 154, thereby being of the same material(s) as the core member 154.

Where the wipers 174 are of a relatively softer material (e.g., with respect to a core member and/or other wipers), the wipers 174 can provide a flushing function to draw fluids away from within the channel. The flushing action can flow ahead and/or behind the wipers 174. Additionally or alternatively, the wipers 174 can further remove debris, soil, and/or residue from the walls of the channel. Additionally or alternatively, the wipers 174 can apply a film of a material (e.g., detergent) that facilitates more effective chemical removal of debris, soil, and/or residue from the walls of the channel. The wiping action of the wipers 174 across the channel wall may smooth any residual soil in the channel into more uniform soil film. A uniform soil surface can be acted on (e.g., enzymatically) more effectively by the detergent introduced in the channel by the flushing function. Other bristle brushes can leave a lumpy soil debris residue that is more difficult for detergents to act on. Additionally or alternatively, the wipers 174 can further apply a film of a lubricant to the walls of the channel.

Figure 9:
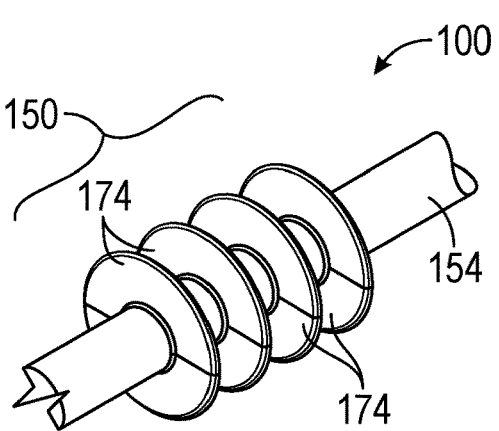
FIG. 9 shows a perspective view of a cleaning section of a cleaning device having monolithic wipers, according to some embodiments of the present disclosure.

FIG. 9 shows a perspective view of a cleaning section of a cleaning device having wipers, according to some embodiments of the present disclosure. As shown in FIG. 9, the cleaning section 150 can include wipers 174, similar to wipers 174 of FIG. 8. However, the wipers can have at least one difference, including size, shape, distribution, and/or material. The wipers 174 can optionally be monolithically formed with the core member 154, thereby being of the same material(s) as the core member 154.

Figure 10:
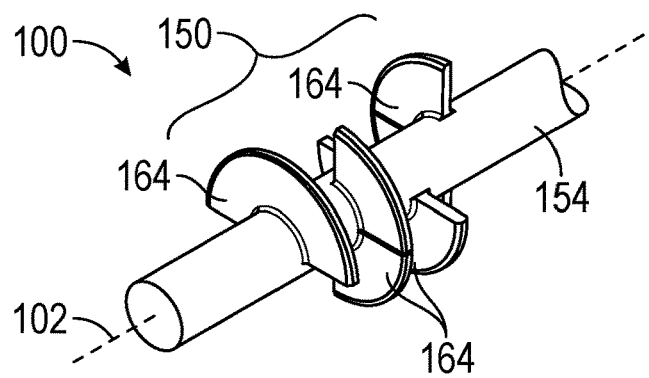
FIG. 10 shows a perspective view of a cleaning section of a cleaning device having wipers extending partially circumferentially, according to some embodiments of the present disclosure.

FIG. 10 shows a perspective view of a cleaning section 150 of a cleaning device 100 having wipers 164, according to some embodiments of the present disclosure. As shown in FIG. 10, each one of multiple wipers 164 can extend radially outwardly from a core member 154. The wipers 164 can provide a cleaning function at least when the cleaning section 150 is moved (e.g., pulled or pushed) longitudinally within a channel of a device. For example, the wipers 164 can apply a force to materials in the channel. The wipers 164 can be monolithically and/or separately formed on the core member 154.

As with the wipers 174 of FIGS. 8 and 9, the wipers 164 can be characterized by their relative width and length. Each wiper 164 can have a width that is greater than the length thereof. However, in contrast to the wipers 174 of FIGS. 8 and 9, the wipers 164 can extend only partially circumferentially (i.e., less than 360°) about the core member 154 and/or the longitudinal axis 102 of the cleaning device 100. For example, from a given longitudinal portion of the core member 154, the wiper 164 can extend in only some radially outward directions on only a radial side thereof. Such a configuration can optionally provide cleaning along an entire inner surface of a channel wall without dividing the channel into separate and longitudinally adjacent portions. Accordingly, fluid (e.g., liquid and/or gas) can be allowed to flow longitudinally around, between, and past the wipers 164, for example to equalize pressure in a blind channel.

The wipers 164 can be distributed longitudinally, such that different wipers 164 extend from the core member 154 at different longitudinal positions along the longitudinal axis of the core member 154. Multiple wipers can be provided for redundant cleaning functions at any given surface portion of a channel. While a certain number of wipers are illustrated in FIG. 10, it will be understood that any number (e.g., 1, 2, 3, 4, 5, 6, 7, 8, 9, 10, or more than 10) of wipers can be provided. The wipers can be evenly or unevenly distributed along the longitudinal axis. More than one wiper 164 can be positioned at a given longitudinal portion of the core member 154. For example, multiple wipers 164 can have a same longitudinal position and be circumferentially spaced apart from each other.

The wipers 164 can be distributed circumferentially, such that different wipers 164 extend from the core member 154 at different circumferential positions (e.g., different radial sides) about the longitudinal axis of the core member 154. The wipers 164 can be staggered in manner that collectively provides full circumferential coverage when the cleaning section 150 is moved longitudinally within the channel. For example, while the wipers 164 are longitudinally spaced apart from each other, the wipers 164 at different longitudinal locations can be circumferentially staggered to only partially overlap each other. Accordingly, at any given surface portion within a channel that overlaps the cleaning section 150, at least one of the wipers 164 will act on the surface portion when the cleaning section 150 is moved longitudinally across that surface portion. At the same time, fluid (e.g., liquid and/or gas) and debris can be allowed to move between and around the wipers 164, for example, when fluid is forced to flow under pressure.

Figure 11:
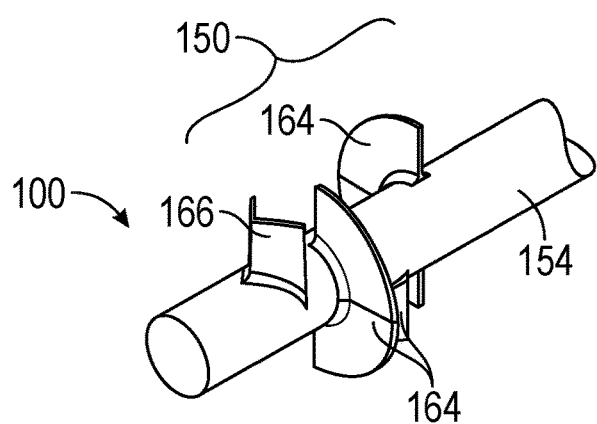
FIG. 11 shows a perspective view of a cleaning section of a cleaning device having wipers and a directional wiper, according to some embodiments of the present disclosure.

FIG. 11 shows a perspective view of a cleaning section of a cleaning device having wipers and a directional wiper, according to some embodiments of the present disclosure.

As shown in FIG. 11, the cleaning section 150 can include wipers 164, similar to wipers 164 of FIG. 10. While the wipers 164 can be generally flat on one or more sides thereof, the cleaning section 150 can further include a directional wiper 166. The directional wiper 166 can have a side that faces in a longitudinal direction and includes at least one surface that is not flat. For example, the directional wiper 166 can form a wedge, plow, or other shape forming an edge. It will be understood that other shapes are contemplated, including a corner, bevel, chamfer, fillet, and the like. The directional feature can be arranged to act on debris, soil, and/or residue by focusing forces on a small region thereof. Accordingly, the directional wiper 166 can have the effect of breaking up an obstruction. Other wipers and/or cleaning features can then provide further cleaning functions with greater efficacy.

Figure 12:
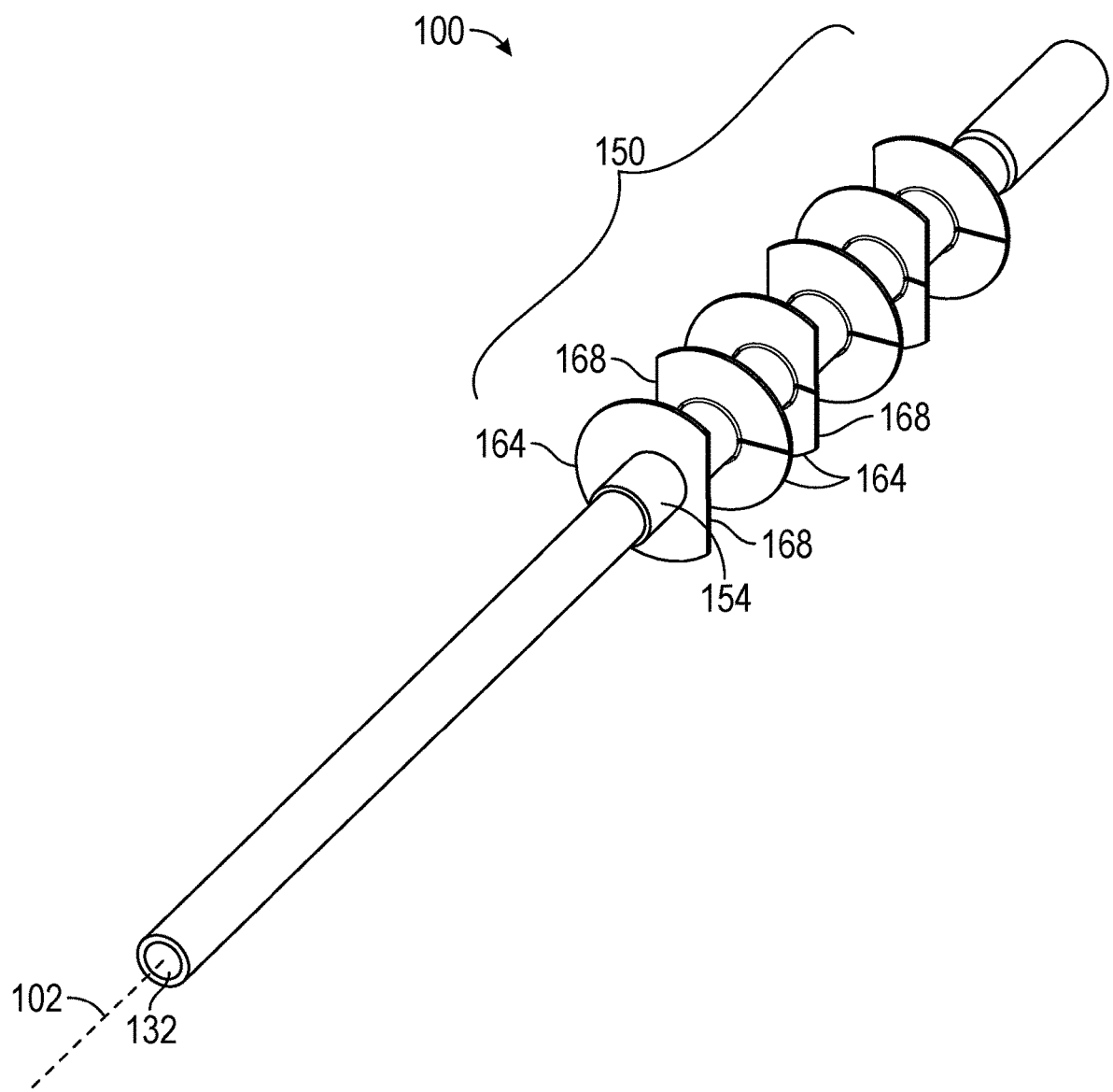
FIG. 12 shows a perspective view of a cleaning section of a cleaning device having wipers with cutout portions, according to some embodiments of the present disclosure.

FIG. 12 shows a perspective view of a cleaning section 150 of a cleaning device 100 having wipers 164, according to some embodiments of the present disclosure. As shown in FIG. 10, each one of multiple wipers 164 can extend radially outwardly from a core member 154. The wipers 164 can provide a cleaning function at least when the cleaning section 150 is moved (e.g., pulled or pushed) longitudinally within a channel of a device. For example, the wipers 164 can apply a force to materials in the channel. The wipers 164 can be monolithically and/or separately formed on the core member 154. Optionally, rather than being monolithically formed together, each of the multiple wipers 164 can be independently bonded to the core member 154, for example in separate molding operations. In such a process, the wipers 164 can optionally be formed from different materials. Optionally, the core member 154 can define a lumen 132 for facilitating flow of a fluid (e.g., liquid and/or gas) there through.

As with the wipers 174 of FIGS. 8 and 9 and the wipers 164 of FIG. 10, the wipers 164 of FIG. 12 can be characterized by their relative width and length. Each wiper 164 can have a width that is greater than the length thereof. However, in contrast to the wipers 164 of FIG. 10, the wipers 164 can extend fully circumferentially (i.e., 360°) about the core member 154 and/or the longitudinal axis 102 of the cleaning device 100, yet still provide openings for fluid (e.g., liquid and/or gas) to travel. For example, while the wipers 164 extend in all directions from the core member 154, each wiper 164 can form a cutout portion 168 relative to a channel into which it is to be inserted. By further example, the cutout portions 168 can be defined by portions of the wipers 164 that extend radially from the core member 154 to a shorter distance than other portions. The cutout portions 168 can be staggered to provide cleaning along an entire inner surface of a channel wall without dividing the channel into separate and longitudinally adjacent portions. Accordingly, fluid can be allowed to flow longitudinally around, between, and past the wipers 164.

Figure 13:
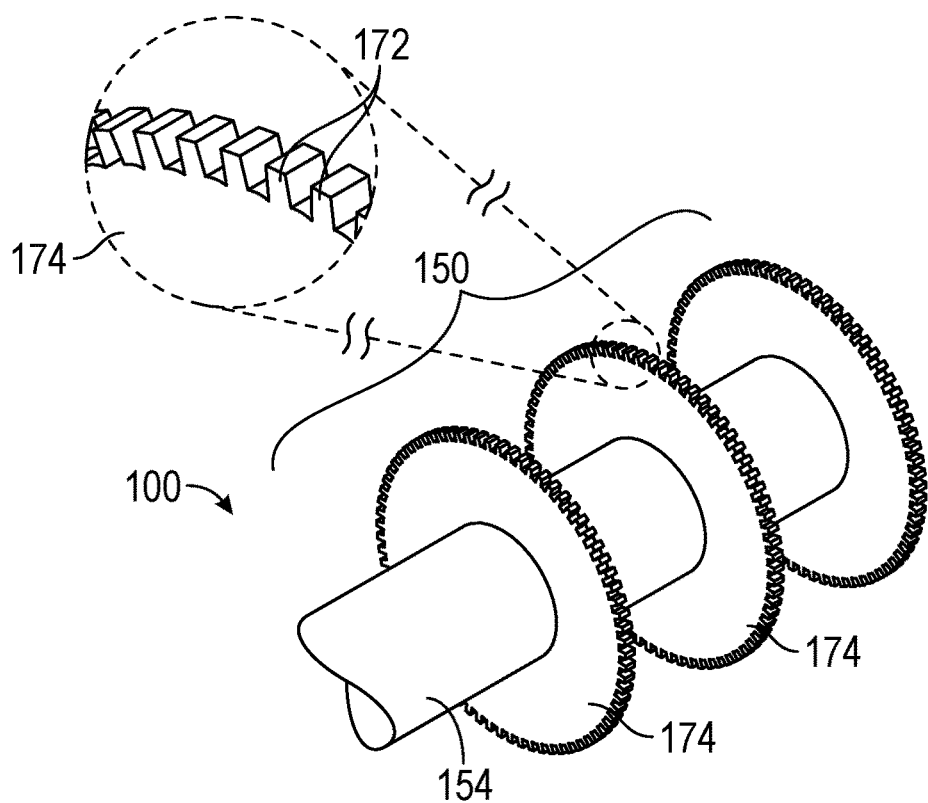
FIG. 13 shows a perspective view of a cleaning section of a cleaning device having wipers with protrusions, according to some embodiments of the present disclosure.

FIG. 13 shows a perspective view of a cleaning section 150 of a cleaning device 100 having wipers 174 with protrusions 172, according to some embodiments of the present disclosure.

As shown in FIG. 13, the cleaning section 150 can include wipers 174, similar to wipers 174 of FIGS. 8 and 9. However, the wipers 174 of FIG. 13 can include a shape at an outer periphery thereof. For example, the wipers 174 can include protrusions 172 that extend radially outward beyond other portions of the wiper 174. By further example, the outer periphery (e.g., radially outward edge) of the wipers 174 can be defined by a pattern shape, such as peaks and troughs, undulations, spikes, waveform patterns (e.g., sinusoidal, triangle wave, square wave, etc.), and the like.

The protrusions 172 of one wiper 174 can be circumferentially staggered relative to protrusions 172 of another wiper 174, so that the protrusions across all wipers 174 collectively provide full circumferential coverage when the cleaning section 150 is moved longitudinally within the channel. Accordingly, any given cavity in a wall can be cleaned by a protrusion 172 of at least one of the wipers 174.

Figure 14:
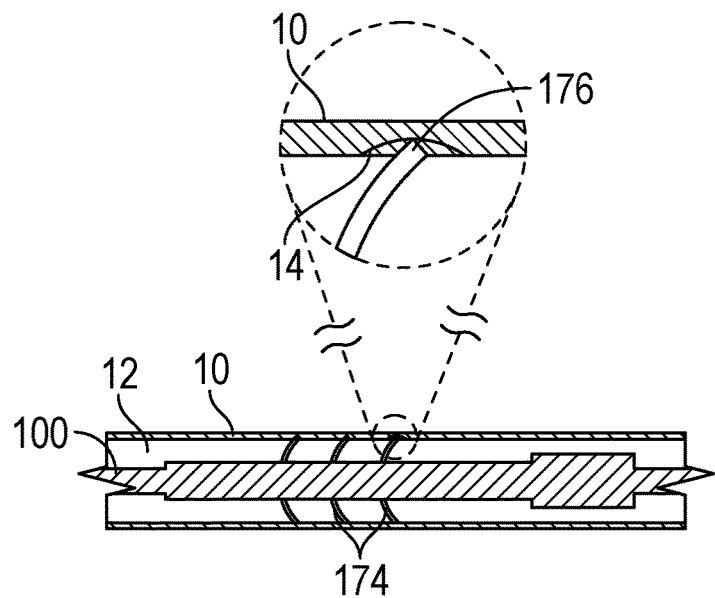
FIG. 14 shows a sectional view of a cleaning device within a channel of a device, according to some embodiments of the present disclosure.

FIG. 14 shows a sectional view of the cleaning device 100 of FIG. 13 within a channel 12 of a device 10, according to some embodiments of the present disclosure. The protrusions 172 can add variety to the outer dimension (e.g., diameter) of the wiper 174. The protrusions can independently bend to conform to the inner wall of a channel to which the cleaning section 150 is applied. The protrusions 172 can be configured to seal against the wall of the channel. For example, whether or not a cavity is present, the protrusions 172 and other portions of the wiper 174 can conform to the shape of the inner wall to substantially seal against the wall.

As shown in FIG. 14, when the wiper 174 encounters a cavity (e.g., scratch, dent, divot, etc.) in the inner wall of the channel, one or more of the protrusions 172 can move into the cavity 14 to providing cleaning therein. Accordingly, the buildup of debris, soil, and/or residue within such cavities 14 can be addressed.

While the protrusions 172 are shown on the wipers 174, it will be understood that the protrusions 172 can be applied to other structures, including the wipers 164 described herein. While the wipers 174 of FIG. 13 are shown as extending fully circumferentially (i.e., 360°) about the core member 154 and extending radially to a range of distances from the core member 154, it will be understood that such protrusions 172 can be formed by other types of wipers and/or fins, such as the wipers of FIGS. 10, 11, and 12 and/or the fins of FIGS. 6 and 7.

FIG. 15 shows a perspective view of a cleaning section 150 of a cleaning device 100 having wipers 174 with staggered supports 175, according to some embodiments of the present disclosure. As shown in FIG. 15, the cleaning section 150 can include wipers 174, similar to wipers 174 of FIGS. 8 and 9. However, the wipers 174 of FIG. 15 can include a shape that provides variable thickness to form staggered supports.

As shown in FIGS. 16 and 17, the wipers 174 can include supports 175 that provide a greater thickness, as measured in an axial direction, than at other (e.g., radially outermost) portions of the wiper 174. The supports 175 can be formed at a relatively radially inner portion of the wiper 174, and other portions of the wiper 174 can form a radially outer portion thereof. The supports 175 can be on one axial side (FIG. 16) or both axial sides (FIG. 17) of the wipers 174. Where the supports 175 are on a single side of the wiper 174, the support 175 can be on a side that faces in a direction of travel of the cleaning device, so that the remaining portion of the wiper 174 is deflected axially away from the support 175.

It will be understood that the support 175 can be formed in one or more of a variety of shapes. For example, as shown in FIGS. 16 and 17, the support 175 can form a generally stepwise transition in thickness. The variations in thickness can be made in other forms, such as one or more of a taper, a curve, and the like. The wipers 174 of any given cleaning section 150 can include those of a single type or multiple types.

By providing wiper 174 with one or more supports 175, the ease of fabrication is increased by improving the ability to fill the wiper in a formation procedure (e.g., molding). While the greater amount of material enhances the ease of fabrication, the flexibility of the wiper is maintained by providing the outer portion of each wiper with the desired lower thickness. As such, both ease of fabrication and the desired performance characteristics are achieved.

In use, the cleaning device can be moved through a channel, where the wipers 174 contact and optionally seal against inner walls of the channel. The outer cross-sectional dimension (e.g., diameter) of the support 175 can be smaller than an inner cross-sectional dimension (e.g., diameter) of the channel into which the cleaning device is inserted. As such, the walls of the channel can be contacted by only the outer portions of the wiper 174, rather than by the support 175. By permitting contact with the thinner portion of the wiper 174, resistance is maintained at an optimal or sufficient level.

Figure 18:
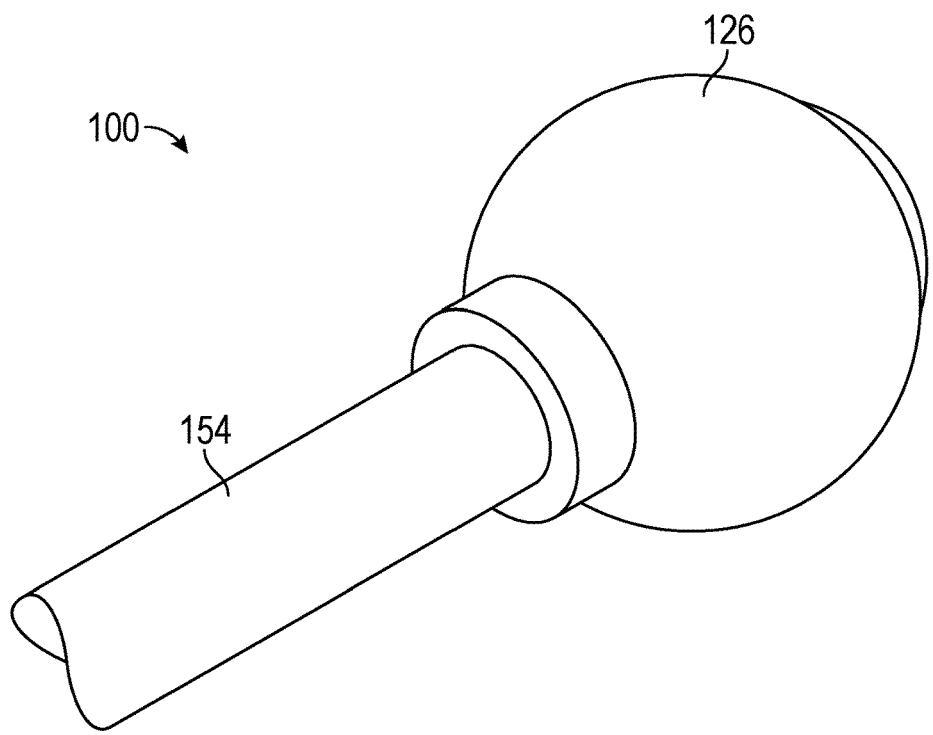
FIG. 18 shows a perspective view of a portion of a cleaning device having a leader, according to some embodiments of the present disclosure.

FIG. 18 shows a perspective view of a portion of a cleaning device having a leader, according to some embodiments of the present disclosure. A leader 126 can form an end portion of a cleaning device 100. The leader 126 can have a rounded or other atraumatic surface. The leader 126 can be of a relatively soft material, as compared to the core member 154 and/or another portion of the cleaning device 100. The leader 126 can provide a soft interface between the core member 154 and the inner wall of a channel to reduce the risk of damage to the wall of the channel. The leader 126 can further facilitate movement of the cleaning device past obstacles in the channel, such as joints between segments, weld lines, discontinuities, and the like.

Figure 19:
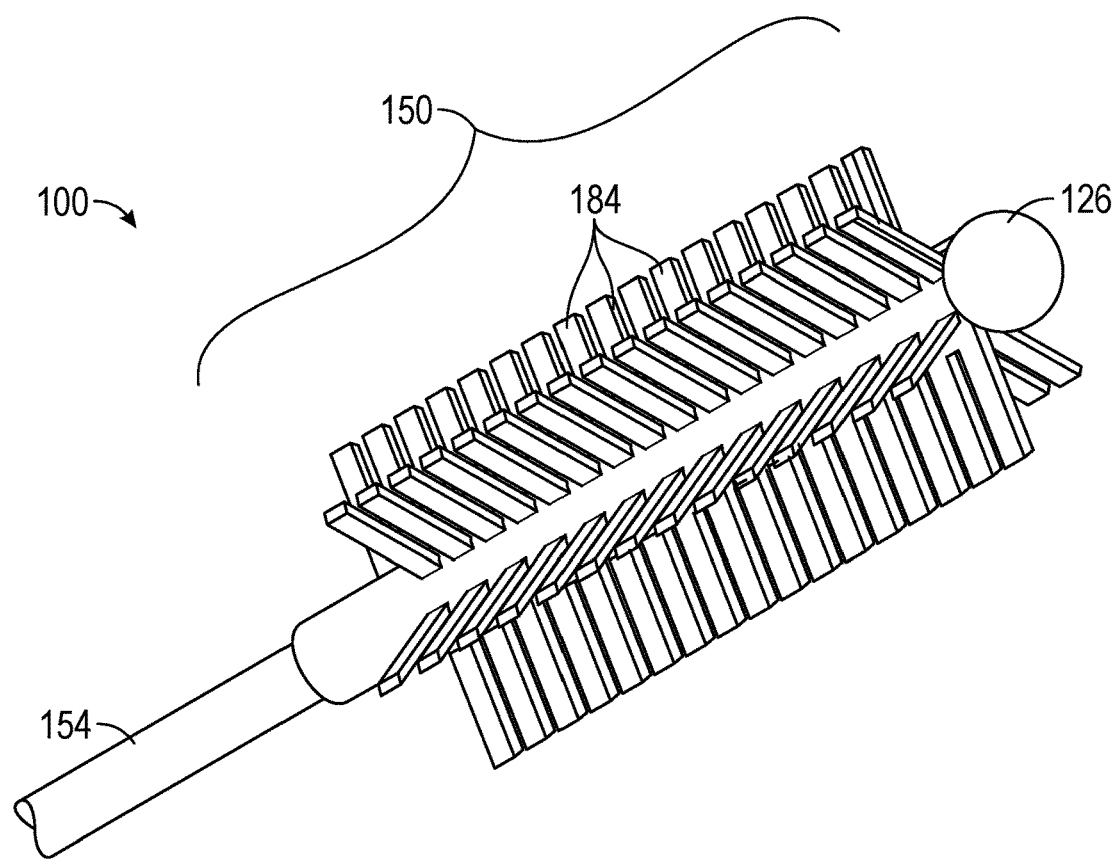
FIG. 19 shows a perspective view of a portion of a cleaning device having a leader and fins, according to some embodiments of the present disclosure.

FIG. 19 shows a perspective view of a portion of a cleaning device having a leader and fins, according to some embodiments of the present disclosure. As shown in FIG. 19, the leader 126 can be monolithically formed with one or more cleaning sections 150, such as a cleaning section 150 having fins 184. For example, both the leader 126 and the features of the cleaning sections 150 can be injection molded onto the core member 154. Accordingly, the leader 126 and the features of the cleaning sections 150 can be of a same material and have similar properties. In some embodiments, the cleaning section 150 and the core member 154 are of the same material, and the leader 126 is of a different material. In some embodiments, the core member 154 and the leader 126 are of the same material, and the cleaning section 150 is of a different material. In some embodiments, the core member 154, the leader 126, and the cleaning section 150 are of the same material. In some embodiments, the core member 154, the leader 126, and the cleaning section 150 are each of a material that is different than that of the others.

Referring now to FIGS. 20-25, a cleaning device can be provided as modules that can be arranged and rearranged in a variety of custom configurations to meet any one of a variety of needs. Each of the cleaning sections described herein can be, include, and/or be combined with any other cleaning section(s) described herein to form a modular cleaning device. For example, any one or more of the cleaning sections described herein can be provided as one or more of the cleaning sections 150A, 150B, and/or 150C of FIG. 20. It will be understood that the embodiments illustrated are examples and that each cleaning device can vary from the features illustrated while still encompassing the features described herein.

As used herein, "modular" or "module" can refer to a characteristic that allows an item, such as a cleaning section, to be connected, installed, removed, swapped, and/or exchanged by a user in conjunction with another item, such as another cleaning section and/or control shaft. Connection of a modular cleaning section with another cleaning section and/or control shaft can be performed and reversed, followed by connection and/or disconnection of another modular cleaning section.

Figure 20:
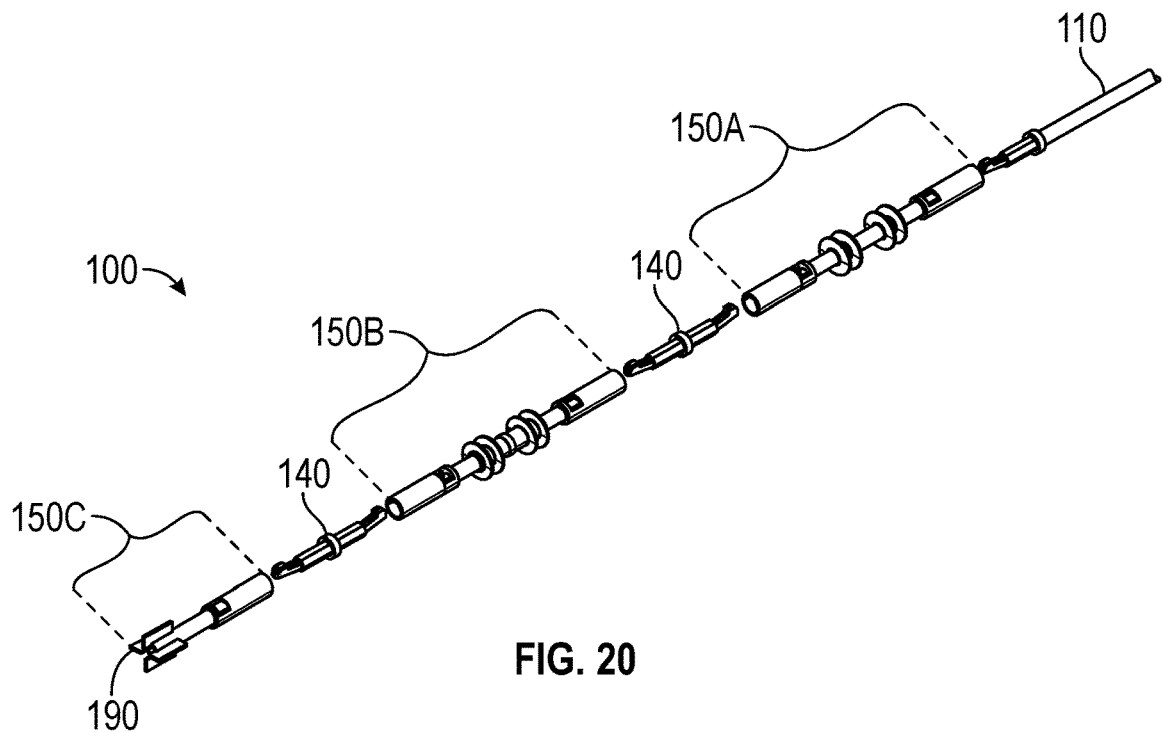
FIG. 20 shows a perspective exploded view of a modular cleaning device having multiple cleaning sections and connectors, according to some embodiments of the present disclosure.

FIG. 20 shows a perspective exploded view of a modular cleaning device having multiple cleaning sections and connectors, according to some embodiments of the present disclosure. As shown in FIG. 20, a cleaning device 100 can include a control shaft 110 connected to one or more cleaning sections (e.g., a first cleaning section 150, a second cleaning section 150B, and/or a third cleaning section 150C, etc.) positioned distal to the control shaft 110. Adjacent pairs of the cleaning sections 150A, 150B, and 150C can be connected to each other by a connector 140 positioned there between, as described further herein.

While three cleaning sections the cleaning sections 150A, 150B, and 150C are illustrated in FIG. 20, it will be understood that any number (e.g., 1, 2, 3, 4, 5, 6, 7, 8, 9, 10, or more than 10) of cleaning sections can be provided. It will be understood that at least one of the cleaning sections can provide at least one feature (e.g., wipers, fins, etc.) that is distinct from a feature (e.g., wipers, fins, etc.) of at least one other cleaning section, as described further herein. Any given cleaning section can be proximal to at least one other cleaning section. Any given cleaning section can be distal to at least one other cleaning section. A cleaning section can be positioned between at least two other cleaning sections.

Figure 21:
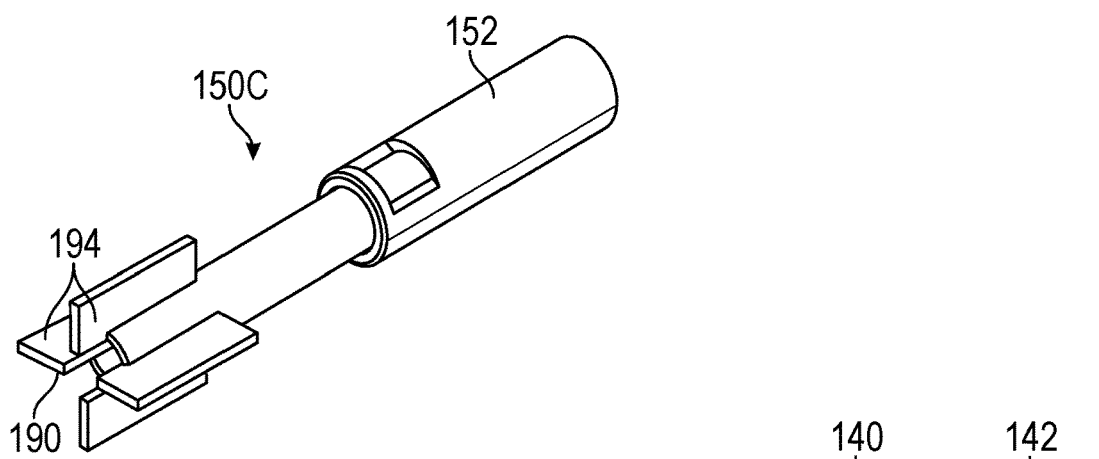
FIG. 21 shows a perspective view of a cleaning section of the cleaning device of FIG. 20, according to some embodiments of the present disclosure.

FIG. 21 shows a perspective view of a cleaning section of the cleaning device of FIG. 20, according to some embodiments of the present disclosure. As shown in FIG. 21, a cleaning section 150C can form a terminal distal end 190, optionally including terminal fins 194. The cleaning section 150C can include a proximal engagement element 152 for engaging another components of the cleaning device.

Figure 22:
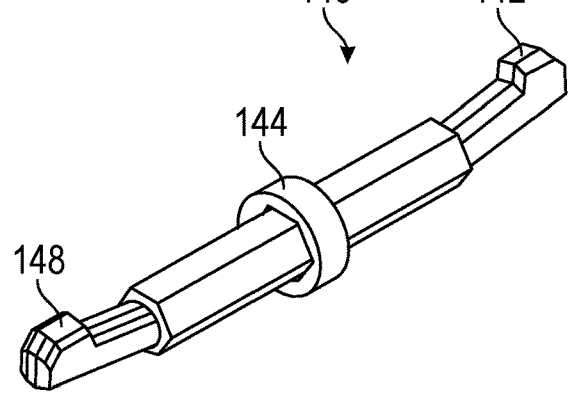
FIG. 22 shows a perspective view of a connector of the cleaning device of FIG. 20, according to some embodiments of the present disclosure.

FIG. 22 shows a perspective view of a connector of the cleaning device of FIG. 20, according to some embodiments of the present disclosure. The connector 140 can include a proximal connector engagement element 142 and a distal connector engagement element 148. A middle portion 144 can be between the proximal connector engagement element 142 and the distal connector engagement element 148. The middle portion 144 can provide a shoulder against which the adjacent sections can abut while locked to the connector 140. The middle portion 144 can optionally be exposed between adjacent cleaning sections or another portion and be flush therewith along the longitudinal length of the cleaning device 100.

Figure 23:
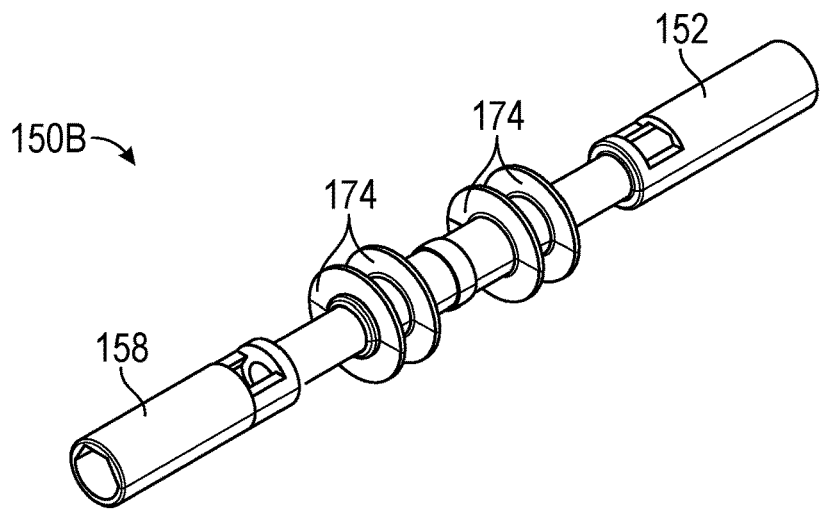
FIG. 23 shows a perspective view of another cleaning section, comprising multiple, separate materials, of the cleaning device of FIG. 20, according to some embodiments of the present disclosure.

FIG. 23 shows a perspective view of another cleaning section of the cleaning device of FIG. 20, according to some embodiments of the present disclosure. The cleaning section 150B can be similar to the cleaning section 150 of FIG. 8, for example, having wipers 174 that are optionally molded onto a core member. The cleaning section 150B can include a proximal engagement element 152 and a distal engagement element 158, each of which being configured to engage a corresponding connector 140.

Figure 24:
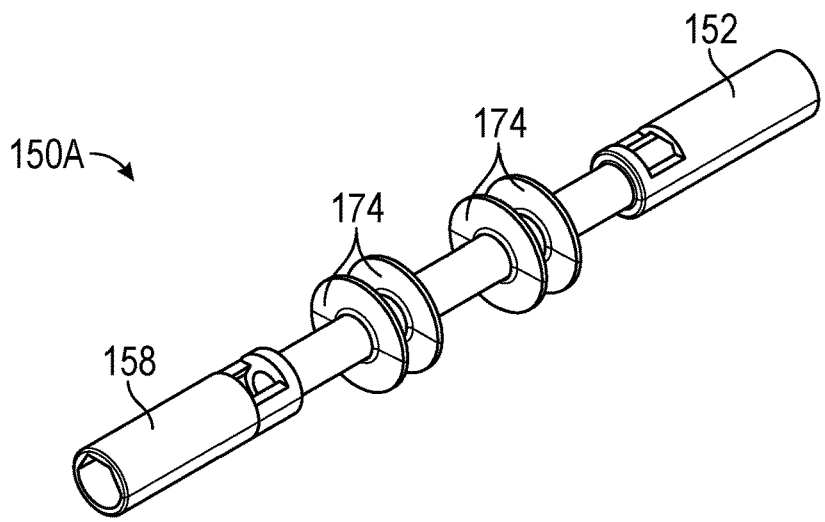
FIG. 24 shows a perspective view of another cleaning section, comprising a single, monolithic material, of the cleaning device of FIG. 20, according to some embodiments of the present disclosure.

FIG. 24 shows a perspective view of another cleaning section of the cleaning device of FIG. 20, according to some embodiments of the present disclosure. The cleaning section 150C can be similar to the cleaning section 150 of FIG. 9, for example, having wipers 174 that are optionally monolithic with a core member. The cleaning section 150C can include a proximal engagement element 152 and a distal engagement element 158, each of which being configured to engage a corresponding connector 140.

Figure 25:
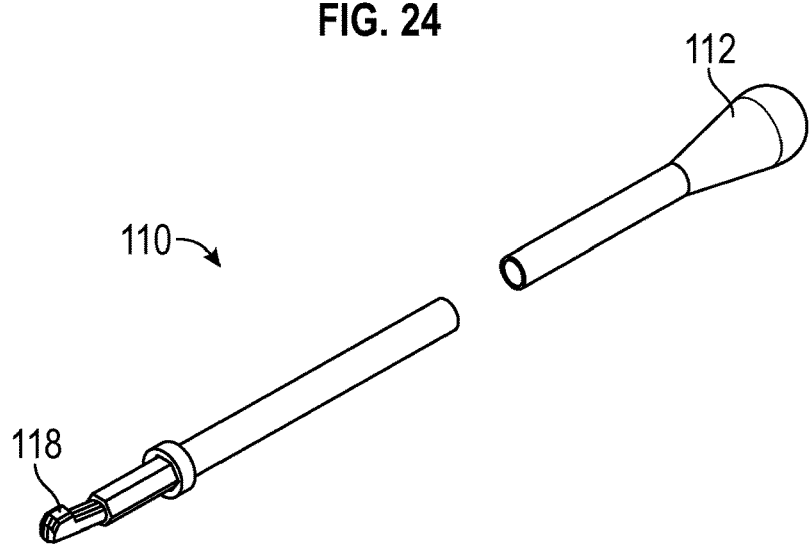
FIG. 25 shows a perspective view of a control shaft of the cleaning device of FIG. 20, according to some embodiments of the present disclosure.

FIG. 25 shows a perspective view of a shaft of the cleaning device of FIG. 20, according to some embodiments of the present disclosure. The control shaft 110 can include a handle 112 or other proximalmost component that allows a user to pull or push the cleaning sections 150A, 150B, and 150C through a channel of a device to clean the inner surfaces thereof. The control shaft 110 can further include a control shaft engagement element 118 for connecting to a proximal engagement element of an adjacent cleaning section.

As shown in FIGS. 21, 23, and 24, the cleaning sections 150A, 150B, and 150C can each include a corresponding proximal engagement element 152 and a corresponding distal engagement element 158. The proximal engagement elements 152 and/or the distal engagement elements 158 can engage portions of the control shaft 110 and/or the connector 140. For example, at least a portion of the control shaft engagement element 118, the proximal connector engagement element 142 and/or the distal connector engagement element 148 can fit within at least a portion of a corresponding engagement element 152 or 158 and mechanical engage (e.g., clip) therein, or vice versa. Such engagement can lock the control shaft 110 and/or the cleaning sections 150A, 150B, and 150C, such that translational and/or rotational movement of the control shaft 110 results in corresponding translational and/or rotational movement of the cleaning sections 150A, 150B, and 150C.

Additional or alternative mechanisms can be provided to lock the control shaft 110 and/or the connectors 140 with respect to the cleaning sections 150A, 150B, and 150C. For example, mechanisms such as locks, latches, snaps, screws, clasps, threads, magnets, pins, an interference (e.g., friction) fit, knurl presses, bayoneting, and/or combinations thereof can be included to lock the control shaft 110 and/or the connectors 140 with respect to the cleaning sections 150A, 150B, and 150C. The control shaft 110 and/or the connectors 140 can remain locked with respect to the cleaning sections 150A, 150B, and 150C until a release mechanism is actuated. The release mechanism can be provided in a manner that is accessible by a user. Where a locking mechanism locks the control shaft 110 and/or the connectors 140 with respect to the cleaning sections 150A, 150B, and 150C, the release mechanism, when actuated, can move and act upon the locking mechanism to cause it to release. For example, the release mechanism, when actuated, can release one or more locks, latches, snaps, screws, clasps, threads, magnets, pins, an interference (e.g., friction) fit, knurl presses, bayoneting, and/or combinations thereof that were previously locking the control shaft 110 and/or the connectors 140 with respect to the cleaning sections 150A, 150B, and 150C.

Figure 26:
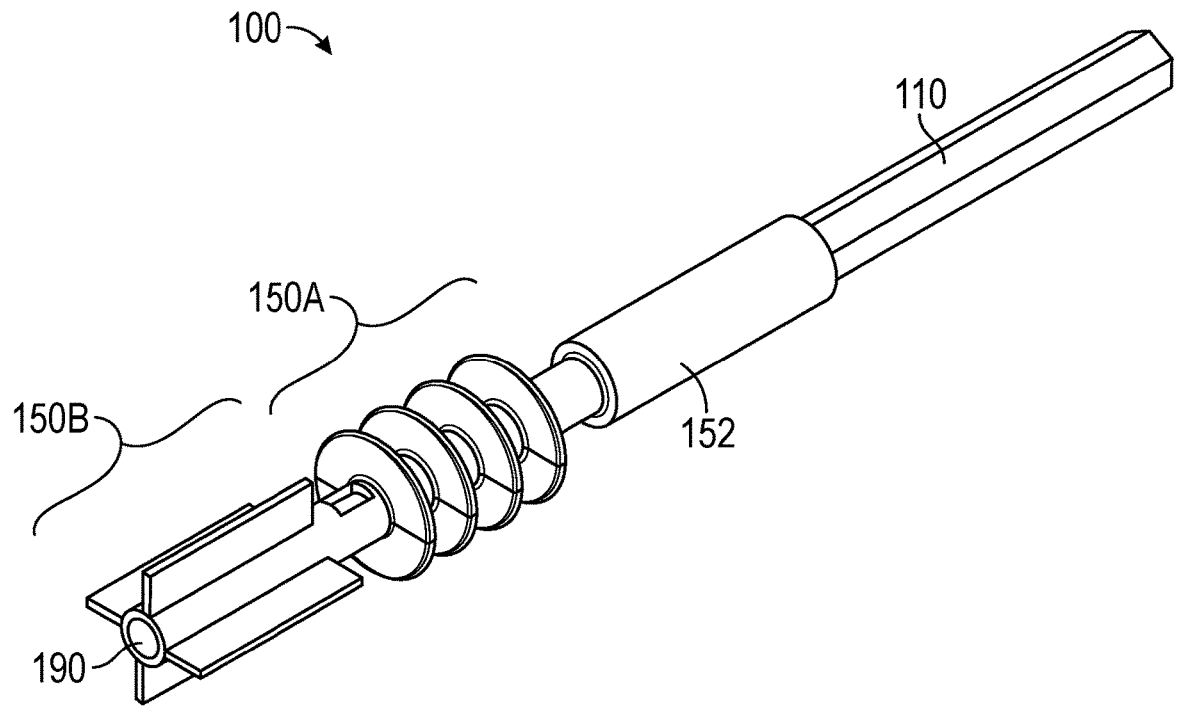
FIG. 26 shows a perspective view of a portion of a cleaning device having a lumen and ports, according to some embodiments of the present disclosure.
Figure 27:
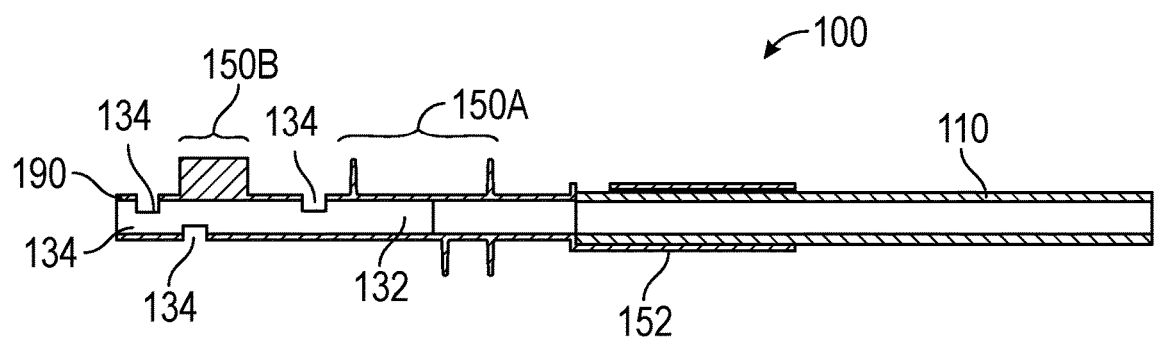
FIG. 27 shows a side sectional view of a cleaning device having a lumen and ports, according to some embodiments of the present disclosure.

Referring now to FIGS. 26 and 27, a cleaning device can be provided with a lumen and ports for providing injection, flow, and/or evacuation of fluids, gas, and/or debris. FIG. 26 shows a perspective view of a portion of a cleaning device having a lumen and ports, according to some embodiments of the present disclosure. FIG. 27 shows a side sectional view of another cleaning device having a lumen and ports, according to some embodiments of the present disclosure.

As shown in FIGS. 26 and 27, a lumen 132 can extend along or parallel to a longitudinal axis of the cleaning device 100, including through at least a portion of a control shaft 110 and/or cleaning sections 150A and 150B. The lumen 132 can extend proximally to provide access to a user and/or another device, such as a fluid control device configured to inject, evacuate, and/or otherwise control flow of fluid (e.g., liquid and/or gas) within the lumen 132. The lumen 132 can extend distally to one or more ports 134 that provide fluid communication between the lumen 132 and a region external to the cleaning device 100. For example, one or more ports can be located proximal to one or more cleaning sections (e.g., cleaning sections 150A and 150B), distal to one or more cleaning sections, between one or more cleaning sections, and/or within one or more cleaning sections. By further example, one or more of the ports 134 can be located between cleaning features (e.g., fins, wipers, etc.) of any given cleaning section. By further example, one or more ports 134 can be located at the terminal distal end 190 of the cleaning device 100.

In use, the lumen 132 and/or the ports 134 can allow fluid (e.g., liquid and/or gas) and/or debris to flow before, during, and/or after moving the cleaning device 100 translationally and/or rotationally within a channel of a device to be cleaned. Where operated actively, the lumen 132 and/or the ports 134 can facilitate injection, flow, and/or evacuation of fluids (e.g., liquid and/or gas) and/or debris by allowing a user to alter pressure conditions within the lumen 132. The lumen 132 and/or the ports 134 can also allow flow to occur passively by providing fluid communication between different regions of the channel in which the cleaning device is positioned. For example, a wiper, fin, or other cleaning feature may separate regions of the channel to be cleaned. Nonetheless, the lumen 132 and/or ports 134 can allow flow to occur by providing fluid communication between the separate regions. When the cleaning device 100 is moved, the lumen 132 and/or ports 134 can allow pressure conditions on opposite sides of the separation to become balanced by facilitating flow. By further example, the lumen 132 and/or the ports 134 can allow pressure to adjust and allow the wipers to reach an end of the terminated and/or blind channel. After a fluid is injected or otherwise present, the wipers can draw any debris and/or fluid out of the channel. The channel can then optionally be closed, for example, with a valve and/or finger.

Figure 28:
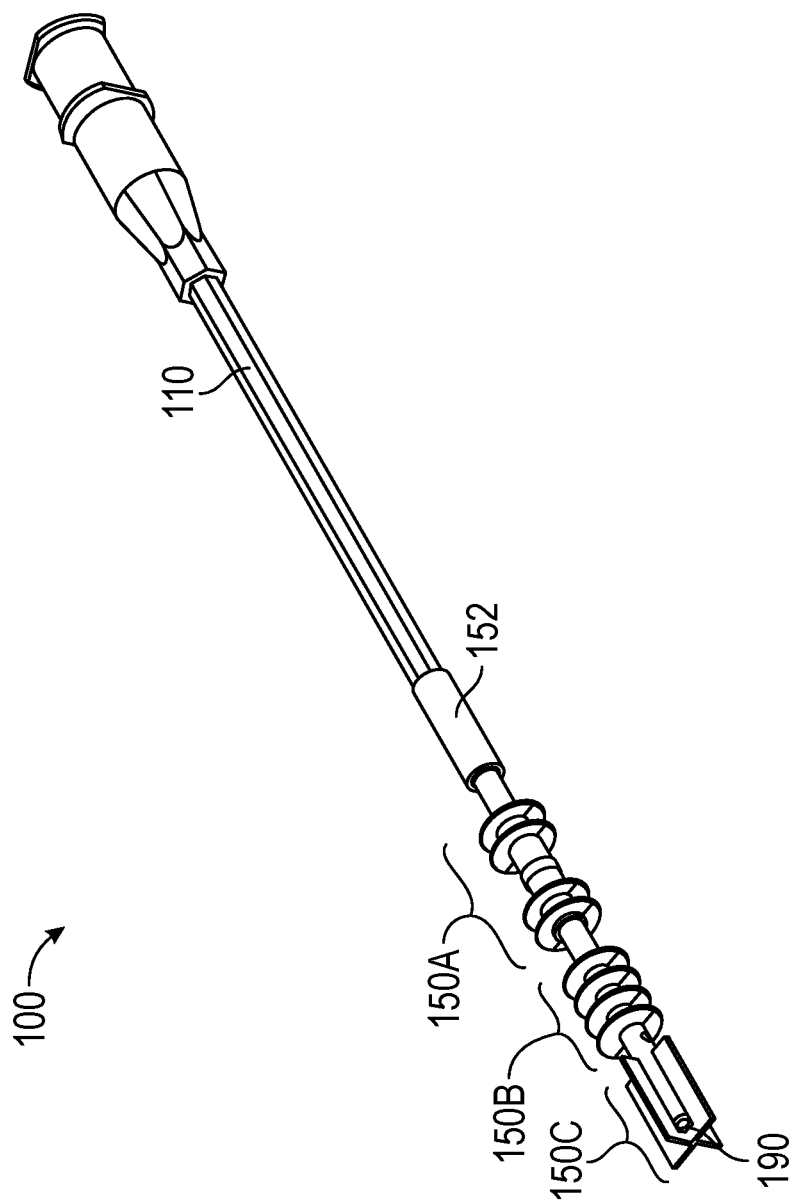
FIG. 28 shows a perspective view of a portion of a cleaning device having a lumen and ports, according to some embodiments of the present disclosure.

Referring now to FIG. 28, a cleaning device can be provided with a lumen and ports across multiple cleaning sections. FIG. 28 shows a perspective view of a portion of a cleaning device having a lumen and ports, according to some embodiments of the present disclosure.

As shown in FIG. 28, a cleaning device 100 can include a control shaft 110 connected to one or more cleaning sections (e.g., a first cleaning section 150, a second cleaning section 150B, and/or a third cleaning section 150C, etc.) positioned distal to the control shaft 110. A lumen can extend across one or more of the cleaning sections, and one or more ports can be provided at, within, between, and/or beyond one or more of the cleaning sections.

As shown in FIG. 28, the control shaft 110 can include a luer lock and/or other interfacing structures for coupling to another device, such as a device to provide injection and/or suction of fluid and/or gas. It will be understood that such an interface can be selected to fit a particular purpose and receive one or more of a variety of other devices. Such an interface can be applied to any of the cleaning devices described herein.

Figure 29:
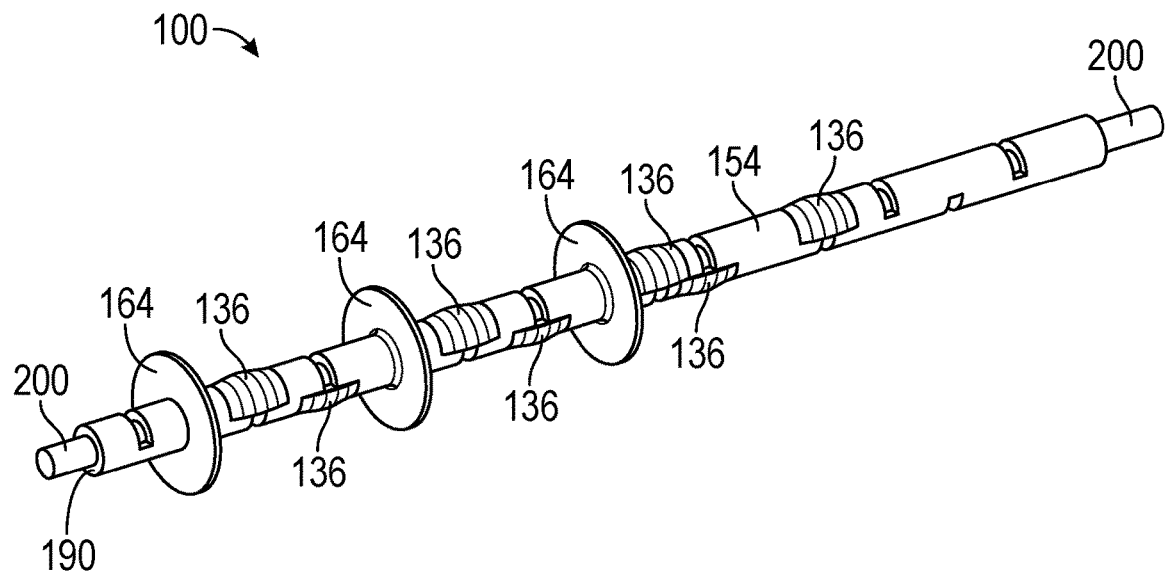
FIG. 29 shows a perspective view of a portion of a cleaning device formed on a filament, according to some embodiments of the present disclosure.
Figure 30:
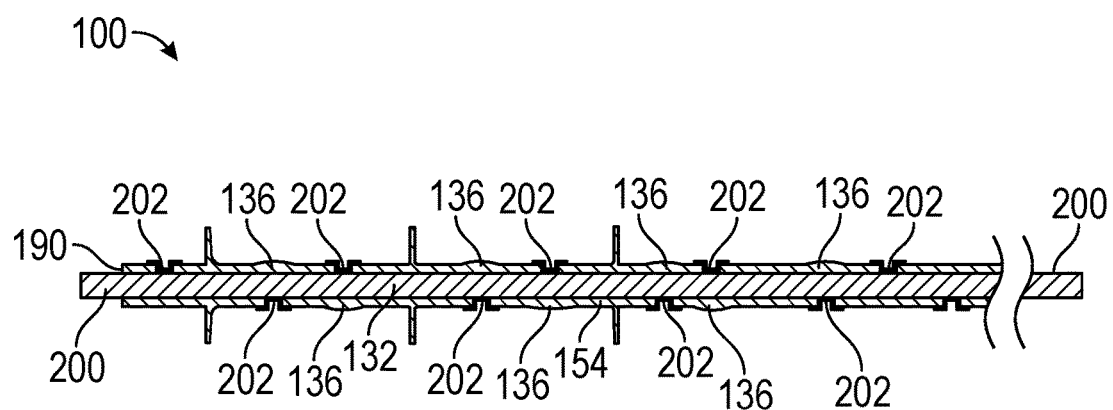
FIG. 30 shows a side sectional view of the cleaning device of FIG. 29, according to some embodiments of the present disclosure.

Referring now to FIGS. 29 and 30, yet another cleaning device can be provided via a molding process. FIG. 29 shows a perspective view of a portion of a cleaning device formed on a filament, according to some embodiments of the present disclosure. FIG. 30 shows a side sectional view of the cleaning device of FIG. 29, according to some embodiments of the present disclosure.

As shown in FIGS. 29 and 30, the cleaning device 100 can be formed, at least in part, about a filament 200. For example, the cleaning device 100, including a core member 154 and/or wipers 164, can be molded onto the filament 200. The cleaning device 100 can be formed with support elements 202 that are applied to the filament 200 to define ports when the cleaning device 100 is formed (e.g., molded). The support elements 202 can be applied to different sides of the filament 200 at different longitudinal locations thereof. The support elements 202 can thereby maintain the filament 200 in a centered position (e.g., within and with respect to an outer mold, not shown). The support elements 202 thereby resist a tendency of the filament 200 to deflect as pressure is applied thereto during an injection molding procedure. By maintaining the filament 200 in a centered position, the core member 154 is provided with a uniform or otherwise intended thickness on radial sides thereof. The support elements 202 can also define ports that extend through the core member 154, as discussed further herein. The cleaning device 100 can be of one or more materials that are optionally different than the material of the filament 200 and/or the support elements 202. The one or more materials of the cleaning device 100 may be formed without bonding to the material of the filament 200 and/or the support elements 202, such that the cleaning device 100 can be removed from the filament 200 and/or the support elements 202 after formation.

The core member 154 can be formed with enlarged regions 136 to facilitate flow of an injected material. For example, each of the enlarged regions 136 can be provided radially opposite a corresponding one of the support elements 202. While the support elements 202 can tend to restrict flow, the enlarged regions 136 can help offset this effect by providing a larger flow path.

Figure 31:
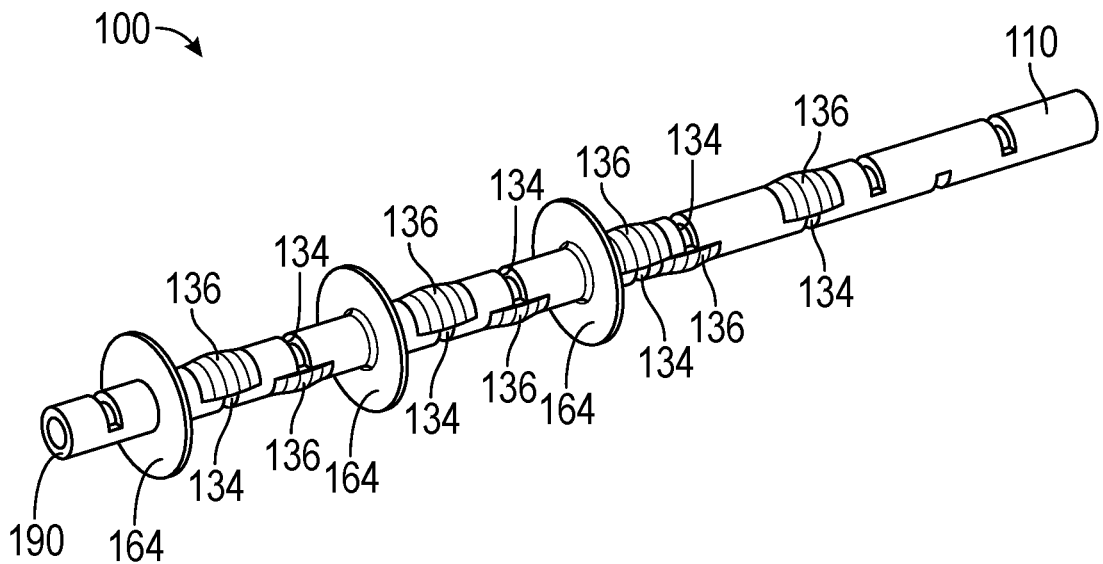
FIG. 31 shows a perspective view of a portion of a cleaning device having a lumen and ports, according to some embodiments of the present disclosure.
Figure 32:
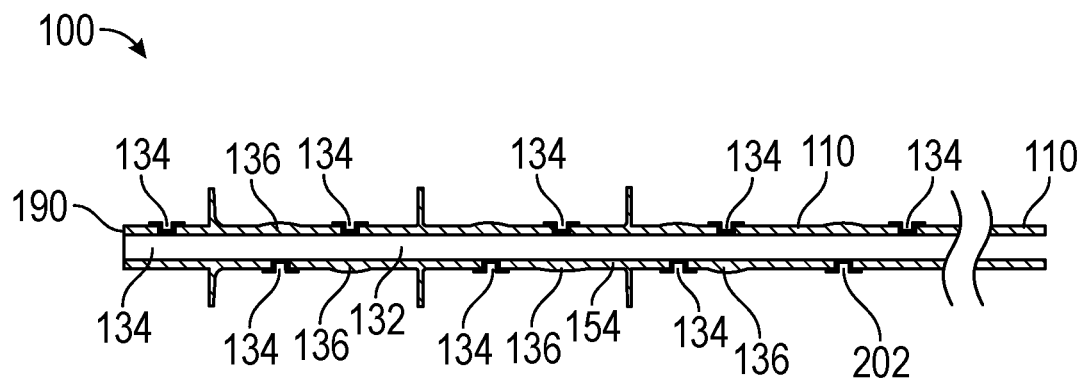
FIG. 32 shows a side sectional view of the cleaning device of FIG. 31, according to some embodiments of the present disclosure.

Referring now to FIGS. 31 and 32, a cleaning device, such as the cleaning device formed as shown in FIGS. 29 and 30, can be provided with a lumen and ports for providing injection, flow, and/or evacuation of fluids and/or debris. FIG. 31 shows a perspective view of a portion of a cleaning device having a lumen and ports, according to some embodiments of the present disclosure. FIG. 32 shows a side sectional view of the cleaning device of FIG. 31, according to some embodiments of the present disclosure.

As shown in FIGS. 31 and 32, a lumen 132 can extend along or parallel to a longitudinal axis of the cleaning device 100, including through at least a portion of a control shaft 110 and/or cleaning sections having wipers 164. By further example, one or more of the ports 134 can be located between cleaning features (e.g., fins, wipers, etc.) of any given cleaning section. By further example, one or more ports 134 can be located at the terminal distal end 190 of the cleaning device 100. Such ports can be formed by a filament and/or support elements during a formation procedure (e.g., injection molding), as described herein. The cleaning device 100 of FIGS. 33 and 34 can be operated as described herein with respect to the cleaning device 100 of FIGS. 26-27.

Figure 33:
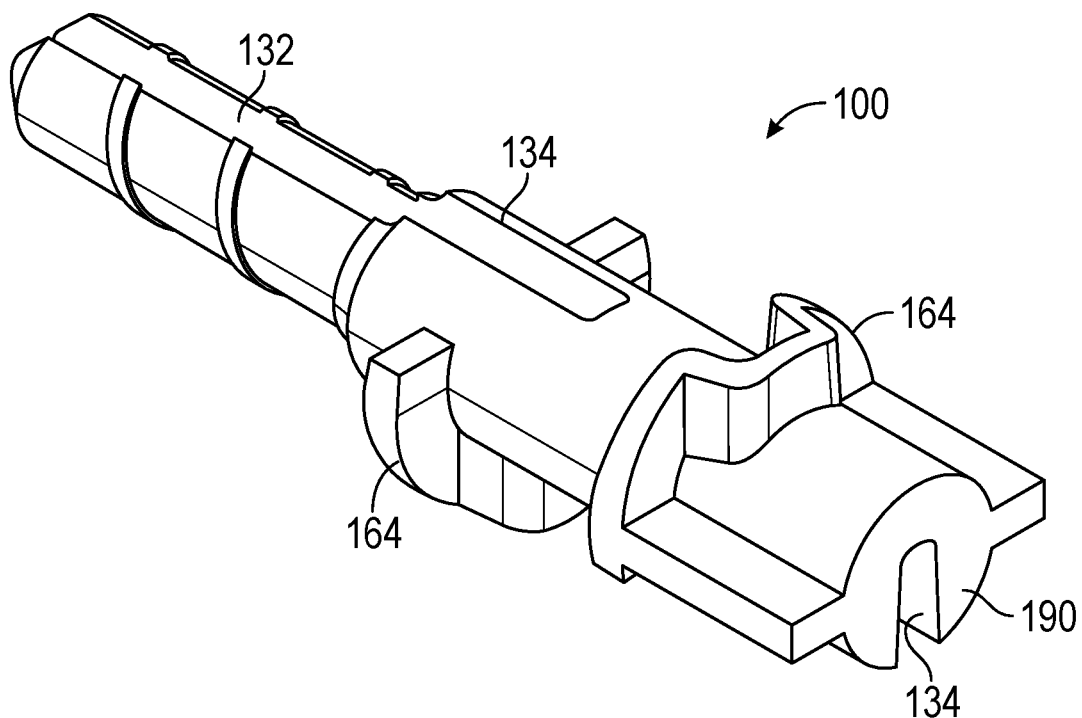
FIG. 33 shows a perspective view of a portion of a cleaning device, according to some embodiments of the present disclosure.
Figure 34:
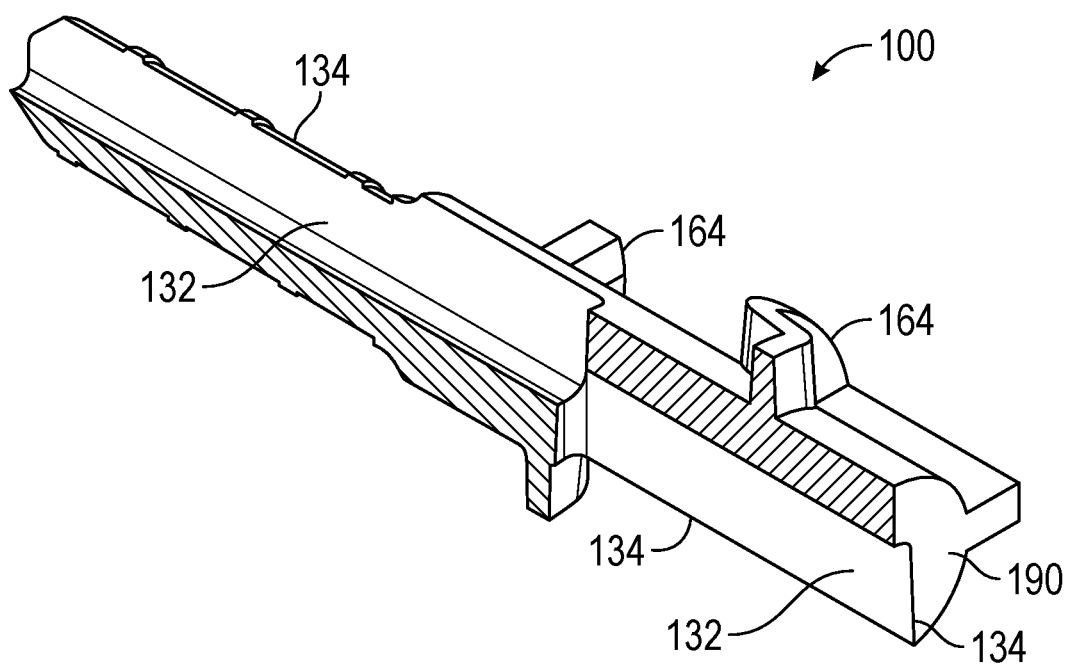
FIG. 34 shows a perspective sectional view of the cleaning device of FIG. 33, according to some embodiments of the present disclosure.

Referring now to FIGS. 33 and 34, yet another cleaning device can be provided via a molding process. FIG. 33 shows a perspective view of a portion of a cleaning device, according to some embodiments of the present disclosure. FIG. 34 shows a perspective sectional view of the cleaning device of FIG. 33, according to some embodiments of the present disclosure.

As shown in FIGS. 33 and 34, a lumen 132 can extend along or parallel to a longitudinal axis of the cleaning device 100, including through, between, and/or on one or more sides of at least a portion of a cleaning section having wipers 164. The lumen 132 can be open along at least a portion thereof by extending to the outer periphery of the cleaning device 100 to form one or more ports 134. As such, the ports 134 can provide fluid communication and exposure to an exterior of the cleaning device 100 along any portion of the length of the lumen 132. The ports 134 can be formed on opposing sides of the cleaning device 100 while still being in fluid communication along an interior region of the lumen 132. At least one of the ports 134 can optionally be formed at a terminal distal end 190 of the cleaning device 100. For example, each of the ports 134 can extend across a side of the cleaning device 100 that is opposite a corresponding wiper 164. Such ports can be formed by a blocking element during a formation procedure (e.g., injection molding). For example, blocking elements, filaments, and/or other mold elements can be provided to form the lumen 132, the ports 134, and the wipers 164 of the cleaning device 100. As such, both the structure and the voids of the cleaning device 100 can be formed in one or more formation (e.g., injection molding) steps. The cleaning device 100 of FIGS. 33 and 34 can be operated as described herein with respect to the cleaning devices 100 of FIGS. 26-27 and 31-32.

Figure 35:
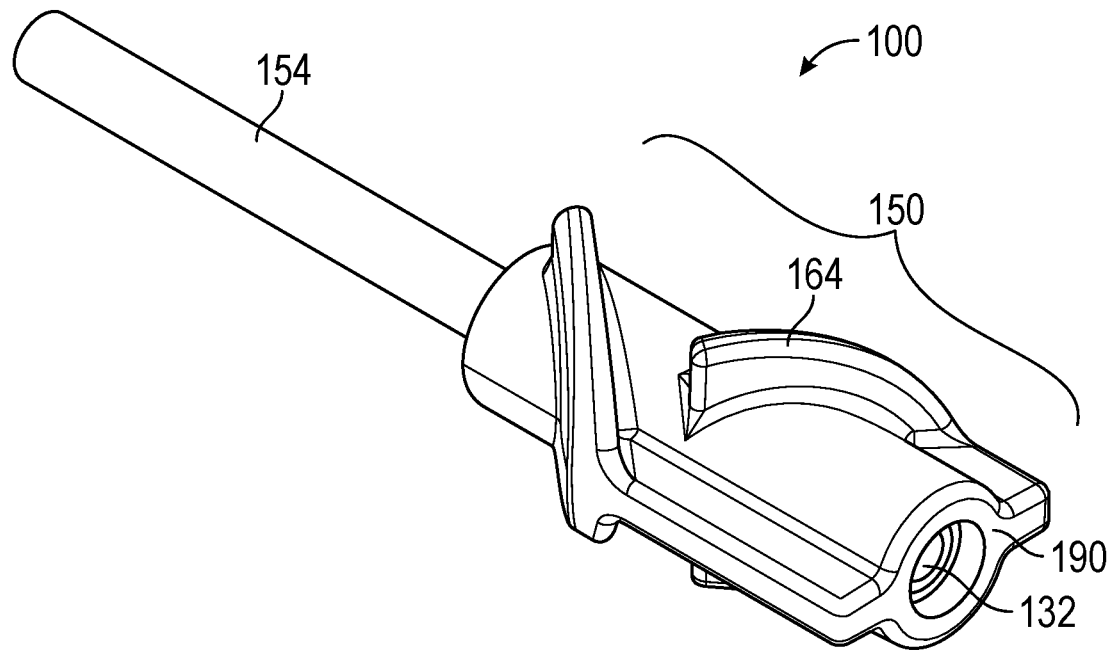
FIG. 35 shows a perspective view of a portion of a cleaning device, according to some embodiments of the present disclosure.
Figure 36:
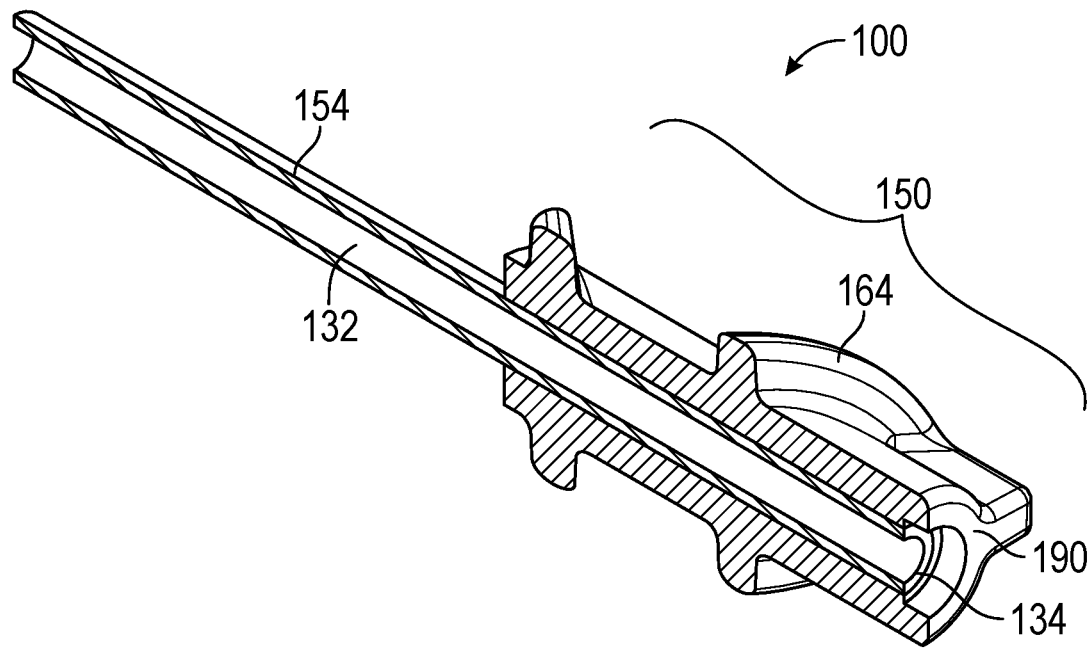
FIG. 36 shows a perspective sectional view of the cleaning device of FIG. 35, according to some embodiments of the present disclosure.

Referring now to FIGS. 35 and 36, yet another cleaning device can be formed from different parts. FIG. 35 shows a perspective view of a portion of a cleaning device, according to some embodiments of the present disclosure. FIG. 36 shows a perspective sectional view of the cleaning device of FIG. 35, according to some embodiments of the present disclosure.

A core member 154 can be or include a tube that allows a mechanical bond with cleaning features (e.g., wipers 164) that are formed thereon. The core member 154 can define a lumen 132 extending there through. The core member 154 can be substantially rigid, for example by being formed, optionally, from metal materials. For example, the core member 154 can provide sufficient stiffness and rigidity to transmit forces and/or torque from a handle to cleaning sections. As shown in FIGS. 35 and 36, a cleaning section 150 can include one or more cleaning features can be formed over the core member 154 at least at a distal end thereof. The cleaning section 150 can be formed by an injection molding process, in which the features of the cleaning section 150 are formed over a corresponding portion of the core member 154 and bonded thereto. Optionally, the core member 154 can optionally be of a harder material, and the cleaning section 150 can be of a softer material. The cleaning section 150 can define a terminal end 190 of the cleaning device 100, such that the terminal end 190 is formed by a relatively soft and/or flexible material.

Figure 41:
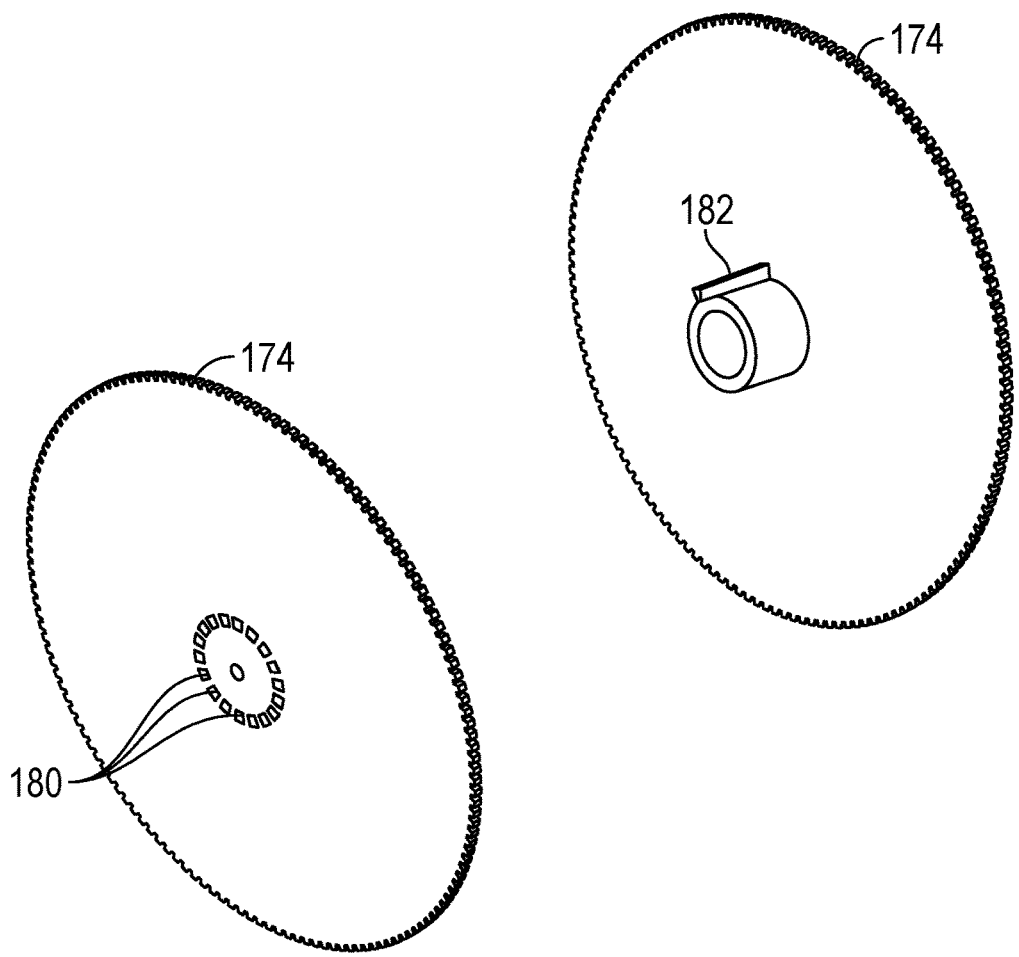
FIG. 41 shows a perspective view of wipers, according to some embodiments of the present disclosure.
Figure 42:
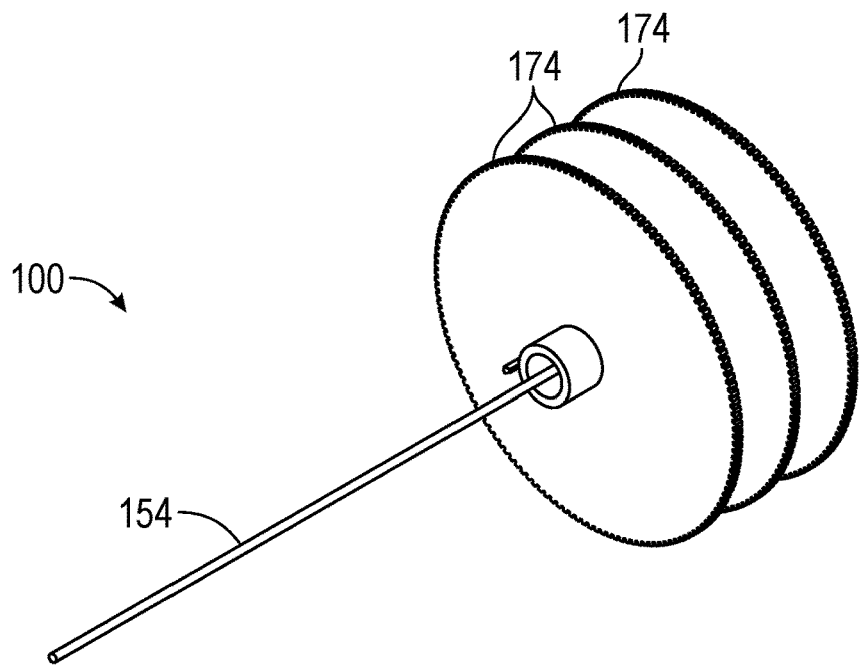
FIG. 42 shows a perspective view of a cleaning device, according to some embodiments of the present disclosure.

Referring now to FIGS. 37-42, yet another cleaning device can be formed from individually selected parts. FIG. 37-40 show a side views of a core member and a wiper in various states of assembly, according to some embodiments of the present disclosure. FIG. 41 shows a perspective view of wipers, according to some embodiments of the present disclosure. FIG. 42 shows a perspective view of a cleaning device, according to some embodiments of the present disclosure.

Figures 37, 38:
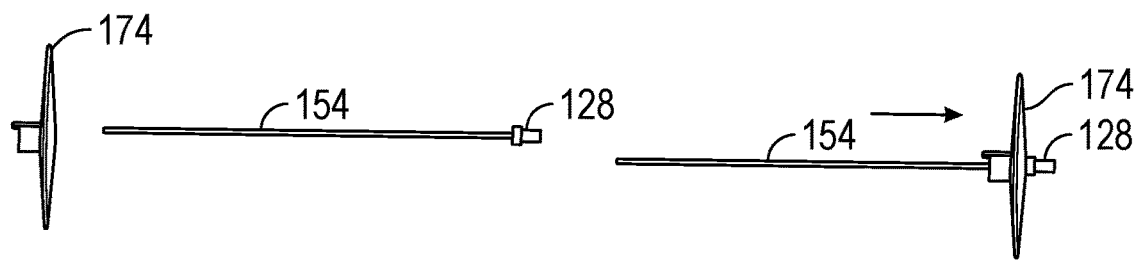
FIG. 37 shows a side view of a core member and a wiper of a cleaning device, according to some embodiments of the present disclosure.
FIG. 38 shows a side view of the cleaning device of FIG. 37 with the wiper attached to the core member, according to some embodiments of the present disclosure.

As shown in FIG. 37, a core member 154 can be or include an elongate member that can receive one or more wipers 174. The core member 154 can include a stopper 128 at a distal end thereof to receive and limit a wiper 174. For example, as shown in FIG. 38, a wiper 174 can be introduced onto the core member 154. The wiper 174 can be slid over or otherwise engaged by the core member 154. The stopper can engage or otherwise abut the wiper 174, such that the wiper 174 is held at distal portion of the core member 154.

Figures 39, 40:
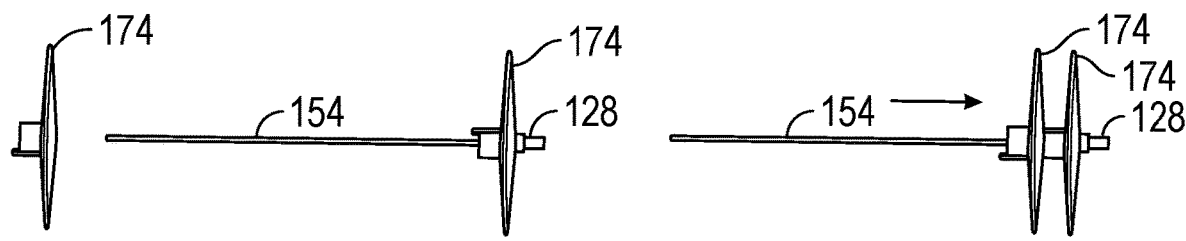
FIG. 39 shows a side view of the cleaning device of FIG. 38 with an additional wiper, according to some embodiments of the present disclosure.
FIG. 40 shows a side view of the cleaning device of FIG. 39 with the wipers attached to the core member, according to some embodiments of the present disclosure.

As shown in FIG. 39, additional wipers 174 can be provided to the core member 154. The additional wiper(s) 174 can be the same or different than preceding wipers 174. As shown in FIG. 40, the additional wiper(s) 174 can also be introduced onto the core member 154. The additional wiper(s) 174 can be slid over or otherwise engaged by the core member 154. The preceding wiper 174 can engage or otherwise abut the additional wiper(s) 174, such that the additional wiper(s) 174 is also held at distal portion of the core member 154. It will be understood that any that any number (e.g., 1, 2, 3, 4, 5, 6, 7, 8, 9, 10, or more than 10) individual wipers 174 can be provided. It will be further understood that at least one of the wipers 174 can optionally provide at least one feature that is distinct from a feature of at least one other wipers 174.

As shown in FIGS. 41 and 42, the wipers 174 can be provided with engagement features that facilitate engagement to each other. For example, one wiper 174 can include a protrusion 182, and another wiper 174 can include one or more openings 180. The protrusion 182 of one wiper 174 can fit within one of the openings 180 of another wiper 174 such that the wipers 174 are secured to maintain a relative position and/or orientation. For example, the engagement of a protrusion 182 and an opening 180 can lock the wipers 174 longitudinally and rotationally. Additional or alternative mechanisms can be provided to lock the wipers 174 with respect to each other. For example, mechanisms such as locks, latches, snaps, screws, clasps, threads, magnets, pins, an interference (e.g., friction) fit, knurl presses, bayoneting, and/or combinations thereof can be included to lock the wipers 174 with respect to each other while on the core member 154.

Referring now to FIGS. 43-45, a dispenser can be used in concert with a cleaning device to provide modular cleaning features. FIG. 43 shows a perspective view of a cleaning device and a dispenser in various states of assembly, according to some embodiments of the present disclosure.

As shown in FIG. 43, a dispenser 300 can include a number of bays 302, each containing a corresponding cleaning section. A cleaning device comprising a handle 112 and a support 116 can be brought to the dispenser 300. The rotational orientation of the dispenser and/or the position of the handle 112 can cause the support 116 to be aligned with a desired one of the bays 302 of the dispenser 300.

As shown in FIG. 44, at least a portion of the support 116 can be inserted into and/or brought near to one of the bays 302. The support 116 can engage a cleaning section 150 within the corresponding bay 302. For example, the support 116 can be rotated to be threaded or otherwise engaged to the cleaning section 150. Additional or alternative mechanisms can be provided to lock the cleaning section 150 with respect to the support 116. For example, mechanisms such as locks, latches, snaps, screws, clasps, threads, magnets, pins, an interference (e.g., friction) fit, knurl presses, bayoneting, and/or combinations thereof can be included to lock the cleaning section 150 with respect to the support 116.

As shown in FIG. 45, the support 116 can be withdrawn from the corresponding bay 302 with the cleaning sections 150 securely attached thereto. For example, the support 116 can be withdrawn with an action or movement that is opposite the insertion, as shown in FIG. 43. The interface 114 of the cleaning device can then be used to attach the cleaning device to a fluid (e.g., liquid and/or gas) supply system, as described further herein.

It will be understood that the support 116 can be returned to the bay 302 from which the cleaning section 150 was supplied or another bay to return and/or release the cleaning section 150. For example, the steps of FIGS. 43-45 can be performed generally in reverse. Another cleaning section 150 can optionally be attached to the support. Such an exchange can be performed when a different type of cleaning device is desired (e.g., for a different cleaning operation and/or target instrument) and/or when a new, unused cleaning section 150 is desired.

Referring now to FIGS. 46-51, a fluid system can be used in concert with a cleaning device and/or handle to provide injection, flow, and/or evacuation of fluids, gas, and/or debris.

Figure 46:
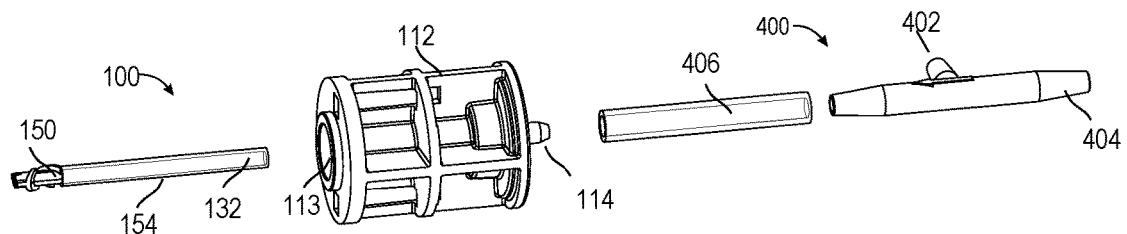
FIG. 46 shows a perspective exploded view of a cleaning device and a fluid system, according to some embodiments of the present disclosure.
Figure 47:
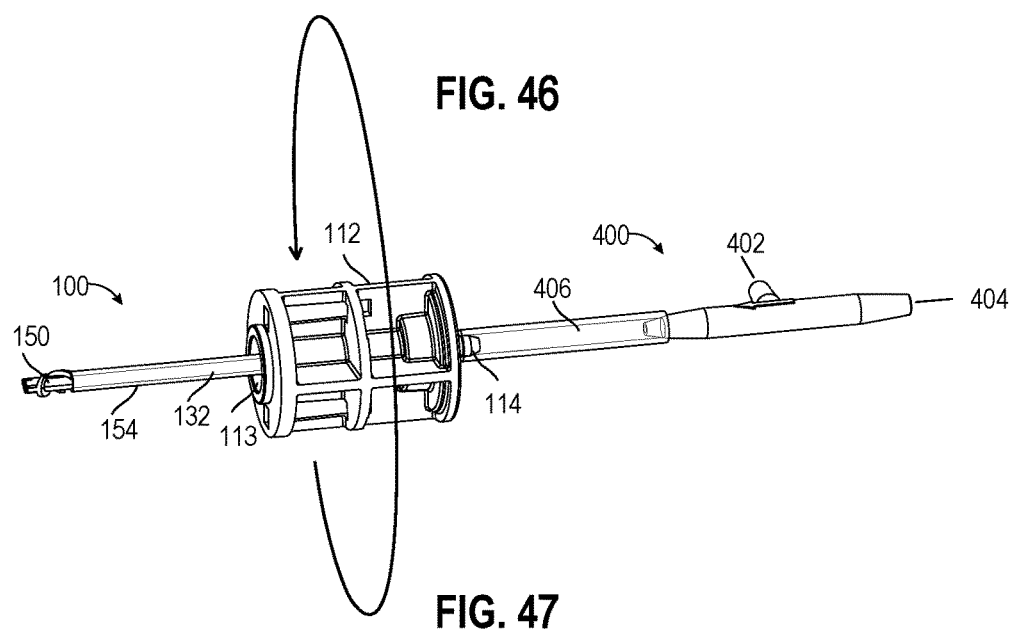
FIG. 47 shows a perspective assembled view of the cleaning device and fluid system of FIG. 46, according to some embodiments of the present disclosure.
Figure 48:
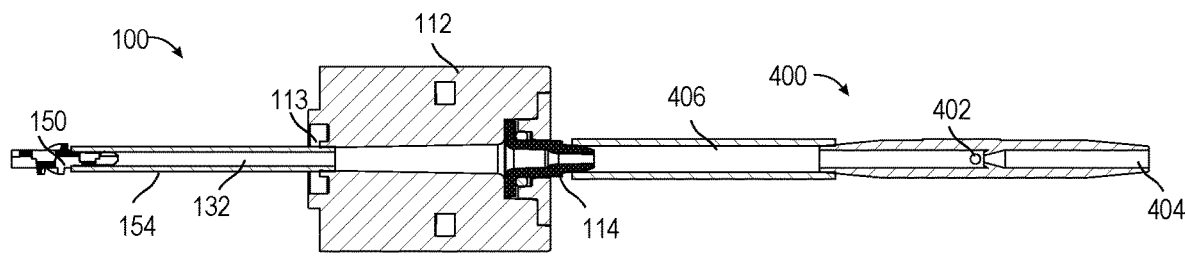
FIG. 48 shows a sectional view of the cleaning device and the fluid system of FIGS. 46 and 47, according to some embodiments of the present disclosure.

FIGS. 46-48 show views of a cleaning device 100, a handle 112, and a fluid system 400, according to some embodiments of the present disclosure. The handle 112 can be one that is used in concert with any one of the cleaning devices described herein. For example, the handle 112 can be securely coupled to a cleaning device for movement, rotation, and/or fluid communication with respect to the cleaning device. The fluid system 400 includes one or more fluid sources, such as a liquid source 402 and/or a gas source 404. Each of the fluid sources can include or be connected to a corresponding fluid storage unit. Each of the fluid sources can be in fluid communication with a fluid line 406 for directing incoming fluids to the handle 112 in a combined flow. The fluids can be delivered to the cleaning device 100 independently, combined, or in sequence depending on the process the end user selects (e.g. cleaning or drying). A combined flow may be used to break up the solid as part of the cleaning action or liquid alone. Gas may be then used to dry the channel as a secondary process. It will be understood that any number (e.g., 1, 2, 3, 4, 5, 6, 7, 8, 9, 10, or more than 10) of fluid sources can be provided to feed into the fluid line 406. It will be further understood that one or more vacuum lines can be fluidly connected to the fluid line 406 to evacuate fluids, gas, and/or debris from the handle 112 and/or a corresponding cleaning device 100.

A cleaning device 100 can be coupled to or include a handle 112 that is configured to support a core member or other support structure of the cleaning device, as described herein. The handle 112 can further provide a grip to facilitate rotation of the cleaning device when torque is applied thereto. Such rotation can enhance cleaning functions by breaking up debris within the instrument acted upon. In particular, when combined with fluid (e.g., liquid and/or gas) delivery, the rotation can effectively loosen and remove debris from the channel being cleaned. The handle 112 can further include an interface 113 that connects to the cleaning device 100 and an interface 114 that connects to the fluid system 400. The interface 114 can provide a secure and sealed connection between the handle 112 and the fluid system 400. The interface 114 can further facilitate rotation of the handle 112 relative to the fluid system 400 while maintaining the connection and fluid flow therefrom. For example, the interface 114 can include a luer lock and/or other interfacing structures for coupling to another device, such as a device to provide injection and/or suction of fluid and/or gas. It will be understood that such an interface can be selected to fit a particular purpose and receive one or more of a variety of other devices. Accordingly, the fluid can flow from the fluid system 400 to the cleaning device 100, including to and/or through any lumens and/or ports thereof.

Figure 49:
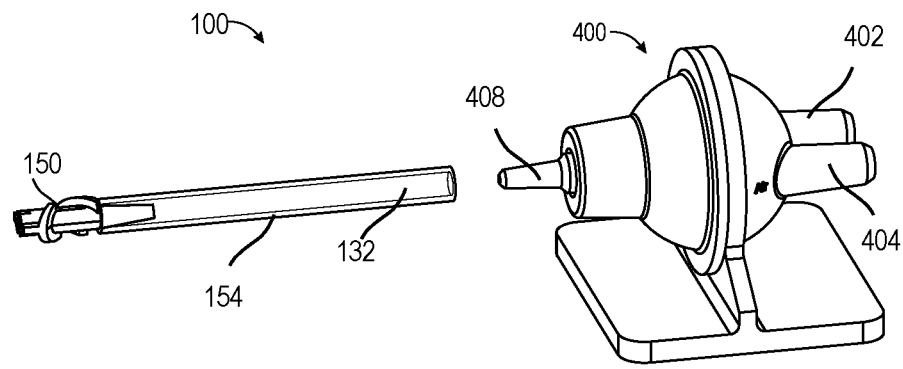
FIG. 49 shows a perspective view of a cleaning device and a fluid system, according to some embodiments of the present disclosure.
Figure 50:
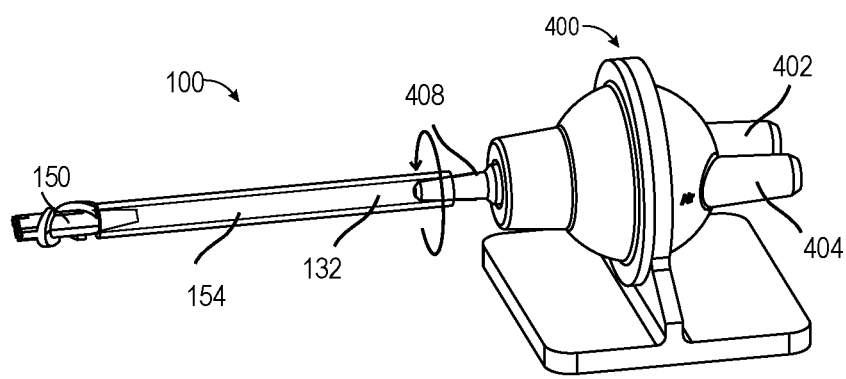
FIG. 50 shows a perspective assembled view of the cleaning device and fluid system of FIG. 49, according to some embodiments of the present disclosure.
Figure 51:
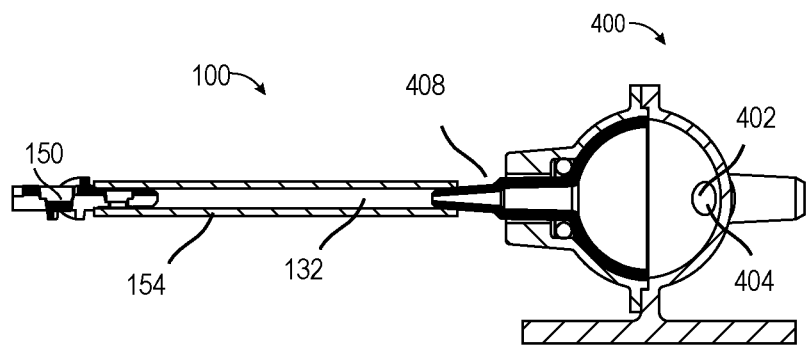
FIG. 51 shows a sectional view of the cleaning device and the fluid system of FIGS. 49 and 50, according to some embodiments of the present disclosure.

FIGS. 49-51 show views of a cleaning device 100 and a fluid system 400, according to some embodiments of the present disclosure. As shown in FIGS. 49-51, an interface 408 can be provided on the fluid system 400, such that the interface 408 provides both the rotational features of the interface 114 described above as well as the functions of the fluid line 406 described above. As such, the cleaning device connected to the fluid system 400 need not provide independent rotational features.

Accordingly, the cleaning devices described herein can provide a hybrid fin and wiper system to facilitate removal of residual solids and liquids from a tubular device (e.g., endoscope), even in a single pass. The removal or cleaning can be clinically sufficient or acceptable in one, two, or more passes. The cleaning devices described herein can provide pressure equalization and release to effectively clean a blind channel without causing hydraulic compaction of debris. The cleaning devices described herein can provide a connection system that facilitates adjustment and customization based on the needs of a particular application.

Various examples of aspects of the disclosure are described below as clauses for convenience. These are provided as examples, and do not limit the subject technology.

Clause A: a cleaning device comprising: a control shaft; a first cleaning section comprising wipers axially offset from each other, each of the wipers extending at least partially circumferentially about a first core member to form a width across the first core member that is greater than a longitudinal length thereof; and a second cleaning section comprising fins, each of the fins extending longitudinally along a second core member to form a longitudinal length that is greater than a width thereof across the second core member.

Clause B: a cleaning device comprising: a control shaft; a first cleaning section comprising first wipers axially offset from each other, each of the first wipers extending entirely circumferentially about a first core member; and a second cleaning section comprising second wipers axially offset from each other, each of the second wipers extending about only a portion of a second core member.

Clause C: a modular cleaning device comprising: a control shaft comprising a control shaft engagement element; a first cleaning section comprising: first cleaning features; a first proximal engagement element configured to releasably engage the control shaft engagement element; and a first distal engagement element; a second cleaning section comprising: second cleaning features; and a second proximal engagement element; and a connector comprising: a proximal connector engagement element configured to releasably engage the first distal engagement element; and a distal connector engagement element configured to releasably engage the second proximal engagement element.

One or more of the above clauses can include one or more of the features described below. It is noted that any of the following clauses may be combined in any combination with each other, and placed into a respective independent clause, e.g., clause A, B, or C.

Clause 1: the wipers are monolithically formed with the first core member.

Clause 2: the wipers are molded over the first core member, the wipers comprising a first material and the first core member comprising a second material having a different hardness than a hardness of the first material.

Clause 3: the first core member and the second core member define a lumen extending at least partially through the first cleaning section and the second cleaning section, the second cleaning section having ports providing fluid communication between the lumen and a space outside the cleaning device.

Clause 4: at least one of the ports is distal to at least one of the wipers.

Clause 5: at least one of the ports is distal to at least one of the fins.

Clause 6: the first cleaning section is between the control shaft and the second cleaning section.

Clause 7: the fins form a distalmost terminal end of the cleaning device.

Clause 8: each of the wipers extends about only a portion of the first core member.

Clause 9: each of the wipers extends entirely circumferentially about the first core member.

Clause 10: each of the first wipers have a width across the first core member that is greater than a longitudinal length thereof; and each of the second wipers have a width across the second core member that is greater than a longitudinal length thereof.

Clause 11: each of the first wipers is molded over the first core member, the first wipers and the first core member being of different materials having different hardnesses; and each of the second wipers is monolithically formed with the second core member.

Clause 12: a third cleaning section comprising fins circumferentially offset from each other.

Clause 13: the first cleaning features comprise wipers.

Clause 14: each of the wipers extends about only a portion of a core member.

Clause 15: each of the wipers extends entirely circumferentially about a core member.

Clause 16: the second cleaning features comprise fins.

Clause 17: the connector is a first connector; the cleaning device further comprises a third cleaning section comprising: third cleaning features; a third proximal engagement element; and a third distal engagement element.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order. It should be understood that the described instructions, operations, and systems can generally be integrated together in a single software/hardware product or packaged into multiple software/hardware products.

In one aspect, a term coupled or the like may refer to being directly coupled. In another aspect, a term coupled or the like may refer to being indirectly coupled.

Terms such as top, bottom, front, rear, side, horizontal, vertical, and the like refer to an arbitrary frame of reference, rather than to the ordinary gravitational frame of reference. Thus, such a term may extend upwardly, downwardly, diagonally, or horizontally in a gravitational frame of reference.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for".

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirements of the applicable patent law, nor should they be interpreted in such a way.

What is claimed is:

1. A cleaning device comprising:
    a control shaft;
    a first cleaning section comprising wipers axially offset from each other, each of the wipers extending at least partially circumferentially about a first length of a core member to form a respective wiper width that is orthogonal to the first length of the core member, the respective wiper width being greater than a respective wiper longitudinal length that is parallel to the first length of the core member; and
    a second cleaning section comprising fins, each of the fins extending longitudinally along a second length of the core member to form a respective fin longitudinal length that is parallel to the second length of the core member, the respective fin longitudinal length being greater than a respective fin width that is orthogonal to the second length of the core member, wherein the first length of the core member and the second length of the core member define a lumen extending at least partially through the first cleaning section and the second cleaning section, the second cleaning section having ports providing fluid communication between the lumen and a space outside the cleaning device.

2. The cleaning device of claim 1, wherein the wipers are monolithically formed with the first length of the core member.

3. The cleaning device of claim 1, wherein the wipers are molded over the first length of the core member, the wipers comprising a first material and the first length of the core member comprising a second material having a different hardness than a hardness of the first material.

4. The cleaning device of claim 1, wherein the first cleaning section is between the control shaft and the second cleaning section.

5. The cleaning device of claim 1, wherein the fins form a distalmost terminal end of the cleaning device.

6. The cleaning device of claim 1, wherein each of the wipers extends about only a portion of the first length of the core member.

7. The cleaning device of claim 1, wherein each of the wipers extends entirely circumferentially about the first length of the core member.

8. A system comprising:
the cleaning device of claim 1;
a fluid system comprising:
one or more inlets for receiving a fluid from a fluid source; and
a fluid line in fluid communication with the one or more inlets; and
a handle comprising:
a first interface for coupling to the fluid line; and
a second interface for coupling to the cleaning device.

9. The system of claim 8, wherein the handle is rotatably coupled to the fluid system, such that rotation of the handle with respect to the fluid system provides rotation of the cleaning device with respect to the fluid system.

10. The cleaning device of claim 1, further comprising a directional wiper extending from the core member and having a surface that faces in a longitudinal direction away from the first cleaning section and the second cleaning section, the surface forming a wedge.

11. A cleaning device comprising:
a control shaft;
a first cleaning section comprising first wipers axially offset from each other, each of the first wipers extending entirely circumferentially about a first length of a core member; and
a second cleaning section comprising at least four second wipers axially offset from each other, each of the second wipers extending about only a portion of a second length of the core member, wherein the at least four second wipers extend from the second length of the core member in respective radial directions that are different from each other.

12. The cleaning device of claim 11, wherein:
each of the first wipers have a width across the first length of the core member that is greater than a longitudinal length thereof; and
each of the second wipers have a width across the second length of the core member that is greater than a longitudinal length thereof.

13. The cleaning device of claim 11, wherein:
each of the first wipers is molded over the first length of the core member, the first wipers and the first length of the core member being of different materials having different hardnesses; and
each of the second wipers is monolithically formed with the second length of the core member.

14. The cleaning device of claim 11, further comprising a third cleaning section comprising fins circumferentially offset from each other.

15. The cleaning device of claim 11, further comprising a directional wiper extending from the core member and having a surface that faces in a longitudinal direction away from the first cleaning section and the second cleaning section, the surface forming a wedge.

16. A cleaning device comprising:
a control shaft;
a first cleaning section comprising first wipers axially offset from each other, each of the first wipers extending entirely circumferentially about a first length of a core member, each of the first wipers being monolithically formed with the first length of the core member;
a second cleaning section comprising second wipers axially offset from each other, each of the second wipers extending about only a portion of a second length of the core member, each of the second wipers being monolithically formed with the second length of the core member; and
a third cleaning section comprising fins, each of the fins extending longitudinally along a third length of the core member to form a respective fin longitudinal length that is parallel to the third length of the core member, the respective fin longitudinal length being greater than a respective fin width that is orthogonal to the third length of the core member, each of the fins being monolithically formed with the third length of the core member.

17. The cleaning device of claim 16, wherein:
each of the first wipers have a width across the first length of the core member that is greater than a longitudinal length thereof; and
each of the second wipers have a width across the second length of the core member that is greater than a longitudinal length thereof.

18. The cleaning device of claim 16, wherein:
each of the first wipers is molded over the first length of the core member, the first wipers and the first length of the core member being of different materials having different hardnesses; and
each of the second wipers is monolithically formed with the second length of the core member.

19. The cleaning device of claim 16, further comprising a directional wiper extending from the core member and having a surface that faces in a longitudinal direction away from the first cleaning section, the second cleaning section, and the third cleaning section, the surface forming a wedge.

* * * * *